United States Patent
Saito

(10) Patent No.: US 8,319,399 B2
(45) Date of Patent: Nov. 27, 2012

(54) ULTRASOUND PROBE

(75) Inventor: Koetsu Saito, Tokyo (JP)

(73) Assignee: Panasonic Corporation, Oskak (JP)

( * ) Notice: Subject to any disclaimer, the term of this patent is extended or adjusted under 35 U.S.C. 154(b) by 839 days.

(21) Appl. No.: 12/447,535

(22) PCT Filed: Nov. 2, 2007

(86) PCT No.: PCT/JP2007/071412
§ 371 (c)(1),
(2), (4) Date: Apr. 28, 2009

(87) PCT Pub. No.: WO2008/056611
PCT Pub. Date: May 15, 2008

(65) Prior Publication Data
US 2010/0066207 A1    Mar. 18, 2010

(30) Foreign Application Priority Data
Nov. 8, 2006 (JP) .................................. 2006-303224

(51) Int. Cl.
*H01L 41/08* (2006.01)
(52) U.S. Cl. ...................................... 310/334; 310/335
(58) Field of Classification Search .................. 310/320, 310/321, 327, 334, 335, 336, 365, 363; 600/437, 600/444, 443, 447, 459, 472; 73/589, 588; H04R 7/00, 17/00; H01L 41/08
See application file for complete search history.

(56) References Cited

U.S. PATENT DOCUMENTS

| | | | | |
|---|---|---|---|---|
| 5,974,884 A | * | 11/1999 | Sano et al. | 73/589 |
| 2003/0187356 A1 | * | 10/2003 | Wakabayashi et al. | 600/437 |
| 2005/0154312 A1 | | 7/2005 | Bruestle | |
| 2005/0261590 A1 | * | 11/2005 | Ogawa et al. | 600/459 |

FOREIGN PATENT DOCUMENTS

| | | |
|---|---|---|
| CN | 1682663 A | 10/2005 |
| DE | 689 18 165 T2 | 1/1995 |

(Continued)

OTHER PUBLICATIONS

International Search Report.

(Continued)

*Primary Examiner* — Thomas Dougherty
*Assistant Examiner* — Karen B Addison
(74) *Attorney, Agent, or Firm* — Pearne & Gordon LLP

(57) ABSTRACT

A technology is disclosed for actualizing an ultrasound probe that can obtain a high-resolution diagnostic image and is highly reliable. In the technology, a piezoelectric element has a predetermined thickness, a ground electrode is formed on one surface in a thickness direction, and a signal electrode is formed on the other surface. When an acoustic matching layer is laminated on a ground electrode formation surface of the piezoelectric element, the acoustic matching layer is configured by a composite material made of a plurality of materials including at least a conductive member. The conductive member has portions penetrating in a layer thickness direction at a plurality of sections on the one electrode formation surface of the piezoelectric element.

22 Claims, 11 Drawing Sheets

FOREIGN PATENT DOCUMENTS

| | | |
|---|---|---|
| DE | 102005051352 A1 | 5/2006 |
| DE | 600 22 651 T2 | 6/2006 |
| EP | 0 346 891 B1 | 9/1994 |
| EP | 1 198 301 B1 | 9/2005 |
| JP | 07-123497 A | 5/1995 |
| JP | 07-037107 U | 7/1995 |
| JP | 08-070498 A | 3/1996 |
| JP | 10-056690 A | 2/1998 |
| JP | 2002-209292 A | 7/2002 |
| JP | 2003-125494 A | 4/2003 |
| JP | 2003-333694 A | 11/2003 |

OTHER PUBLICATIONS

Applicant's Comments in response to Views Report from the International Searching Authority.

German Office action dated Sep. 7, 2010 for Appl. No. 11 2007 002 645.6-35.

Chinese Office action for CN 200780041233.4 dated Aug. 12, 2011.

* cited by examiner

ULTRASOUND PROBE

TECHNICAL FIELD

The present invention relates to an ultrasound probe used to obtain diagnostic information on a subject by being placed in contact with the subject, and transmitting and receiving ultrasonic waves.

BACKGROUND ART

An ultrasonic diagnostic apparatus irradiates a biological subject, such as a human or an animal, with ultrasonic waves. The ultrasonic diagnostic apparatus detects echo signals reflected within the subject and displays a tomogram of in vivo tissue, thereby providing information required to diagnose the subject. In the ultrasonic diagnostic apparatus, an ultrasound probe is used to transmit the ultrasonic waves into the subject and to receive the echo signals from within the subject.

FIG. 9 is a cross-sectional view of a configuration example of a conventional ultrasound probe of this type. In FIG. 9, to transmit and receive ultrasonic waves to and from a subject (not shown), an ultrasound probe 30 includes a plurality of piezoelectric elements 11, an acoustic matching layer 12 (12a and 12b) that is one layer or more (two layers in FIG. 9), an acoustic lens 13, an electrical terminal 15 for signals, a backing material 14, and an electrical terminal 16 for grounding. The piezoelectric elements 11 are unidirectionally arrayed (a direction perpendicular to paper surface in FIG. 9). The acoustic matching layer 12 is provided on a surface of the piezoelectric elements 11 on a subject side (upper side in FIG. 9) (a surface on the subject side will, hereinafter, be referred to as a front surface). The acoustic lens 13 is provided on the front surface of the acoustic matching layer 12. The electrical terminal 15 for signals is provided on a surface of the piezoelectric elements 11 on a side opposite to the subject side (lower side in FIG. 9) (a surface on the side opposite to the subject side will, hereinafter, be referred to as a back surface). The backing material 14 is provided on the back surface of the electrical terminal 15 for signals. The electrical terminal 16 for grounding is mounted between a first acoustic matching layer 12a and a second acoustic matching layer 12b.

A piezoelectric element 11 is made of a piezoelectric ceramic, such as lead zirconate titanate (PZT), a monocrystal, or a composite piezoelectric material that is a combination of the piezoelectric ceramic, the monocrystal, and a high-polymer material. Alternatively, the piezoelectric element 11 is made of a piezoelectric material made of a high-polymer material, represented by polyvinylidene fluoride (PVDF), and the like. An electrode is formed on the front surface and on the back surface of the piezoelectric elements 11. Electrical signals are transmitted and received between the electrodes and the piezoelectric elements 11. In other words, the piezoelectric elements 11 convert voltage into ultrasonic waves and transmit the ultrasonic waves into the subject. The piezoelectric element 11 also receives echoes reflected within the subject and converts the echoes into electrical signals.

The acoustic matching layer 12 is provided to efficiently transmit the ultrasonic waves to the subject and receive the ultrasonic waves from the subject. More specifically, the acoustic matching layer 12 serves to bring an acoustic impedance of the piezoelectric element 11 closer to an acoustic impedance of the subject in stages. In the example shown in FIG. 9, the first acoustic matching layer 12a and the second acoustic matching layer 12b are laminated to form the acoustic matching layer 12. Graphite, which is a conductive member, is used as the first acoustic matching layer 12a. The electrical terminal 16 is taken out from the front surface of the first acoustic matching layer 12a, the electrical terminal 16 being an insulating film on which a metal film is deposited. Furthermore, the second acoustic matching layer 12b is provided on the front surface of the electrical terminal 16. In this configuration, the insulating film does not easily break, even should the piezoelectric elements 11 break as a result of mechanical impact from an external source or the like. Therefore, electrical conductivity can be ensured and, as a result, reliability is high (refer to, for example, Patent Document 1, below).

On the other hand, a configuration is also known that achieves a broader band of frequency through use of a material having a higher acoustic impedance than graphite as the first acoustic matching layer 12a (refer to, for example, Patent Document 2, below).

Moreover, a configuration of the first acoustic matching layer 12a is also known in which a through-hole is provided on a portion of an insulating member. A conductive member is fitted into the through-hole, thereby connecting the electrical terminal provided on the front surface of the first acoustic matching layer 12a and the piezoelectric elements 11 provided on the back surface of the first acoustic matching layer 12a (refer to, for example, Patent Document 3, below).

The acoustic lens 13 serves to focus an ultrasonic beam to increase resolution of a diagnostic image. The acoustic lens 13 is an optional element, provided as required. The backing material 14 is connected so as to hold the piezoelectric elements 11, and further serves to attenuate unnecessary ultrasonic waves.

Patent Document 1: Japanese Patent Application Publication No. H07-123497
Patent Document 2: Japanese Patent Application Publication No. 2003-125494
Patent Document 3: Japanese Utility Model Application Publication No. H07-37107

In an electronic scan type ultrasonic diagnostic apparatus, the piezoelectric elements form a plurality of groups. The ultrasonic diagnostic apparatus drives each piezoelectric element group with a certain amount of delay time between there. The ultrasonic diagnostic apparatus then transmits the ultrasonic waves into the subject from each piezoelectric element group and receives echo signals from within the subject. As a result of the delay time being provided in this way, the ultrasonic beam is focused or dispersed, allowing an ultrasonic image that has a wide field of view or a high resolution to be obtained.

A system in which a plurality of piezoelectric element groups are given a constant amount of delay time and an ultrasonic image is obtained is already known as a common system. A broader band of frequency is essential in the ultrasound probe for obtaining a high-resolution ultrasonic image, such as that described above. Moreover, while high resolution is desired, the ultrasound probe is also required to have a slim form to enhance operability because the ultrasonic probe is operated by a doctor or a laboratory technician, and the diagnostic image is obtained by the ultrasound probe coming into direct or indirect contact with the subject. During operation and other instances, the ultrasound probe may become broken as a result of being accidentally dropped or struck. Therefore, high reliability against breakage is also required.

As a measure for achieving a broader band of frequency in the ultrasound probe, a configuration is given in which the acoustic matching layer provided on the front surface of the piezoelectric elements is three or more layers, as described in Patent Document 2. However, in this configuration, silicon, which is a semiconductor, is used in a first acoustic matching layer on the piezoelectric element side. Therefore, the electrical terminal taken out from the electrode of the piezoelectric elements on the first acoustic matching layer side can only be taken out from a portion of an end section of the electrode formed on the piezoelectric elements. Therefore, in this configuration, when the piezoelectric elements and the electrode break as a result of mechanical impact, disconnection occurs upon breaking, and functions deteriorate.

On the other hand, in the configuration described in Patent Document 1, graphite, which is conductive, is used as the first acoustic matching layer. The electrical terminal is provided on the front surface of the first acoustic matching layer, the electrical terminal being an insulating film on one main surface of which a metal film is deposited. Therefore, reliability is high. However, the conductive material used in the first acoustic matching layer has low acoustic impedance. Moreover, the acoustic matching layer can only be laminated to include two layers. Therefore, a broader band of frequency is difficult to achieve. Ultrasound probes of recent years tend to have broader bands. Diagnosis is often performed by a high-resolution ultrasonic image being obtained through use of second or third harmonic content of a fundamental frequency, or through use of a plurality of frequencies. Therefore, achieving a broader band of frequency is becoming increasingly important.

DISCLOSURE OF THE INVENTION

The present invention has been achieved in light of the above-described issues. An object of the present invention is to provide an ultrasound probe that can obtain a high-resolution diagnostic image and is highly reliable. Another object of the present invention is to provide an ultrasound probe that has excellent operability.

In an ultrasound probe of the present invention including a piezoelectric element on which an electrode is formed on both surfaces in a thickness direction, and an acoustic matching layer laminated on one electrode formation surface of the piezoelectric element, the acoustic matching layer is configured by a composite material made of a plurality of materials including at least a conductive member. The conductive member has portions penetrating in a layer thickness direction at a plurality of sections on the one electrode formation surface of the piezoelectric element.

As a result of the configuration, an acoustic impedance of the acoustic matching layer laminated on the one electrode formation surface of the piezoelectric element can be set to a desired value. Therefore, frequency band can be broadened, thereby allowing a high-resolution, diagnostic image to be obtained. The electrical terminal can be connected at a plurality of areas on the one electrode formation surface of the piezoelectric element through the acoustic matching layer. Therefore, a highly reliable ultrasound probe is provided.

In the present invention, the acoustic matching layer is configured by a composite material made of a plurality of materials including an insulating member or semiconductive member and a conductive member, or a composite material made of a plurality of materials including the insulating member or semiconductive member and a plurality of materials including the conductive member. In addition, the conductive member has portions penetrating in a layer thickness direction at a plurality of sections on the one electrode formation surface of the piezoelectric element.

As a result of the configuration, an acoustic impedance of the acoustic matching layer laminated on the one electrode formation surface of the piezoelectric element can be set to a desired value. Therefore, frequency band can be broadened, thereby allowing a high-resolution, diagnostic image to be obtained. The electrical terminal can be connected at a plurality of areas on the one electrode formation surface of the piezoelectric element through the acoustic matching layer. Therefore, a highly reliable ultrasound probe is provided.

In an ultrasound probe of the present invention including a plurality of piezoelectric elements having a predetermined thickness, on which an electrode is formed on both surfaces in a thickness direction, and which are disposed in a direction perpendicular to the thickness direction, and a plurality of acoustic matching layers laminated on one electrode formation surface of the plurality of piezoelectric elements, the acoustic matching layer includes a first acoustic matching layer and a second acoustic matching layer successively laminated on the piezoelectric elements. The first acoustic matching layer is configured by a composite material made of a plurality of materials including an insulating member or semiconductive member and a conductive member. The conductive member has portions penetrating in a layer thickness direction at a plurality of sections on the one electrode formation surface of the piezoelectric element.

As a result of the configuration, the acoustic impedance can be easily set to a desired value because the acoustic matching layer has multiple layers. Therefore, a high-resolution, diagnostic image can be obtained. The electrical terminal can be connected at a plurality of areas on the one electrode formation surface of the piezoelectric element through the first acoustic matching layer. Therefore, a highly reliable ultrasound probe is provided.

In the present invention, in the composite material configuring the acoustic matching layer adjacent to the piezoelectric element, the insulating member or semiconductive member and the conductive member are disposed in predetermined areas.

As a result of the configuration, volume amounts of the insulating member or semiconductive member and the conductive member can be arbitrarily set. The acoustic impedance can be easily decided.

In the present invention, an electrical terminal that is laminated on an outer surface section of the acoustic matching layer adjacent to the piezoelectric element is included. In the electrical terminal, a conductive film is deposited on one main surface of an insulating film. The electrical terminal is laminated such that the one main surface of the insulating film faces the acoustic matching layer. The conductive film is electrically connected to one electrode formed on the piezoelectric element, via the conductive member configuring the acoustic matching layer.

As a result of the configuration, the insulating film does not easily break even when the piezoelectric element and the one electrode break as a result of mechanical impact and the like. Therefore, malfunctions caused by disconnection become rare. An ultrasound probe with excellent operability is provided.

In an ultrasound probe of the present invention including a plurality of piezoelectric elements having a predetermined thickness, on which an electrode is formed on both surfaces in a thickness direction, and which are disposed in a direction perpendicular to the thickness direction, and a plurality of acoustic matching layers laminated on one electrode formation surface of the plurality of piezoelectric elements, with n as an integer of three or more, the acoustic matching layer includes a first to n-th acoustic matching layers successively laminated on the piezoelectric elements. An electrical terminal is inserted between the first acoustic matching layer and a second acoustic matching layer. At least the first acoustic matching layer is configured by a composite material made of a plurality of materials including an insulating member or semiconductive member and a conductive member. The conductive member has portions penetrating in a layer thickness direction at a plurality of sections on the one electrode formation surface of the piezoelectric elements. In the electrical terminal, a conductive film is deposited on an insulating film. The electrical terminal is laminated such that one main surface of the insulating film faces the acoustic matching layer. The conductive film is electrically connected to one electrode formed on the piezoelectric element, via the conductive member configuring the first acoustic matching layer.

As a result of the configuration, the acoustic matching layer has multiple layers, and the acoustic impedance of the acoustic matching layer can be set to a desired value. Therefore, a high-resolution, diagnostic image can be obtained. The electrical terminal can be connected at a plurality of areas on the one electrode formation surface of the piezoelectric element through the first acoustic matching layer. Therefore, reliability can be enhanced. Moreover, because the insulating film does not easily break, malfunctions caused by disconnection become rare. An ultrasound probe with excellent operability is provided.

In an ultrasound probe of the present invention including a plurality of piezoelectric elements having a predetermined thickness, on which an electrode is formed on both surfaces in a thickness direction, and which are disposed in a direction perpendicular to the thickness direction, and a plurality of acoustic matching layers laminated on one electrode formation surface of the plurality of piezoelectric elements, with n as an integer of three or more, the acoustic matching layer includes a first to n-th acoustic matching layers successively laminated on the piezoelectric elements. An electrical terminal is inserted between the second acoustic matching layer and a third acoustic matching layer. At least the first acoustic matching layer and the second acoustic matching layer is configured by a composite material made of a plurality of materials including an insulating member or semiconductive member and a conductive member. The conductive member has portions penetrating in a layer thickness direction at a plurality of sections on the one electrode formation surface of the piezoelectric elements. In the electrical terminal, a conductive film is deposited on an insulating film. The electrical terminal is laminated such that one main surface of the insulating film faces the acoustic matching layer. The conductive film is electrically connected to one electrode formed on the piezoelectric element, via the conductive member configuring the first acoustic matching layer and the conductive member configuring the second acoustic matching layer.

As a result of the configuration, the acoustic matching layer has multiple layers, and the acoustic impedance of the acoustic matching layer can be set to a desired value. Therefore, a high-resolution, diagnostic image can be obtained. The electrical terminal can be connected at a plurality of areas on the one electrode formation surface of the piezoelectric element through the first and second acoustic matching layers. Therefore, reliability can be enhanced. Moreover, because an insulating film is used that does not easily break even by mechanical impact and the like, an ultrasound probe with excellent operability is provided.

In the present invention, in the composite material configuring the first acoustic matching layer, the insulating member or semiconductive member and the conductive member are disposed in predetermined areas.

As a result of the configuration, volume amounts of the insulating member or semiconductive member and the conductive member in the composite material configuring the first acoustic matching layer can be arbitrarily set. The acoustic impedance can be easily decided.

In the present invention, in the composite material configuring the second acoustic matching layer, the insulating member or semiconductive member and the conductive member are disposed in predetermined areas.

As a result of the configuration, volume amounts of the insulating member or semiconductive member and the conductive member in the composite material configuring the second acoustic matching layer can be arbitrarily set. The acoustic impedance can be easily decided.

In the present invention, with a thickness direction of the piezoelectric element as a Z direction, a direction perpendicular to the Z direction as an X direction, and a direction perpendicular to the Z direction and the X direction as a Y direction, the composite material configuring the acoustic matching layer has any one coupled structure among a coupled structure in which the conductive member has a connection in only the Z direction and has no connection in the X and Y directions, and the insulating member or semiconductive member has a connection in three directions, X, Y, and Z, a coupled structure in which the conductive member has a connection in two directions, Y and Z, and the insulating member or semiconductive member has a connection in two directions, Y and Z, or a coupled structure in which the conductive member has a connection in three directions, X, Y, and Z, and the insulating member or semiconductive member has a connection in only the Z direction and has no connection in the X and Y directions.

As a result of the configuration, volume amounts of the insulating member or semiconductive member and the conductive member in the composite material configuring the acoustic matching layer can be easily set. The portions in which the conductive member penetrates in a layer thickness direction at a plurality of sections on the one electrode formation surface of the piezoelectric elements can be easily formed.

In an ultrasound probe of the present invention including a piezoelectric element having a predetermined thickness and on which an electrode is formed on both surfaces in a thickness direction, and an acoustic matching layer laminated on one electrode formation surface of the piezoelectric element, the acoustic matching layer is configured by a composite material made of a plurality of materials including at least a conductive member. The conductive member has portions penetrating in a layer thickness direction at a plurality of sections on the one electrode formation surface of the piezoelectric element. The conductive member is configured such that a volume amount is a continuous gradient in a thickness direction or the volume amount changes in stages.

As a result of the configuration, the acoustic impedance of the acoustic matching layer laminated on the one electrode formation surface of the piezoelectric element can be set to a desired value. Therefore, frequency band can be broadened, thereby allowing a high-resolution, diagnostic image to be obtained. The electrical terminal can be connected at a plurality of areas on the one electrode formation surface of the piezoelectric element through the acoustic matching layer. Therefore, a highly reliable ultrasound probe is provided.

In the present invention, the composite material made of the plurality of materials of the acoustic matching layer is configured by a material including an insulating member or semiconductive member and a conductive member.

As a result of the configuration, the acoustic impedance of the acoustic matching layer laminated on the one electrode formation surface of the piezoelectric element can be set to a desired value. In addition, the acoustic matching layer can be multiple layers. Therefore, frequency band can be broadened, thereby allowing a high-resolution, diagnostic image to be obtained. The electrical terminal can be connected at a plurality of areas on the one electrode formation surface of the piezoelectric element through the acoustic matching layer. Therefore, a highly reliable ultrasound probe is provided.

In the present invention, the conductive member in the composite material includes at least one of metal, a composite of metal and a high-polymer material, and carbide of graphite.

As a result of the configuration, the material can be selected also taking into consideration the acoustic impedance.

In the present invention, the insulating member or semiconductive member in the composite material is at least one of glass, ceramics, quartz crystal, a composite of organic polymer and metal, and a monocrystal or polycrystal silicon.

As a result of the configuration, the acoustic impedance can be easily decided.

In the present invention, the acoustic matching layer laminated on the one electrode formation surface of the piezoelectric element is configured by the composite material made of the plurality of materials including the insulating member or semiconductive member and the conductive member. Therefore, the acoustic impedance can be set to a desired value. As a result, the frequency band can be broadened, thereby allowing a high-resolution, diagnostic image to be obtained. The conductive member has portions penetrating in the layer thickness direction at a plurality of sections on the one electrode formation surface of the piezoelectric element. As a result, the electrical terminal can be connected at a plurality of areas on the one electrode formation surface of the piezoelectric element through the acoustic matching layer. Therefore, a highly reliable ultrasound probe is provided.

BEST MODE FOR CARRYING OUT THE INVENTION

Preferred embodiments of the present invention will be described in detail with reference to the accompanying drawings.

<First Embodiment>

Figure 1A:
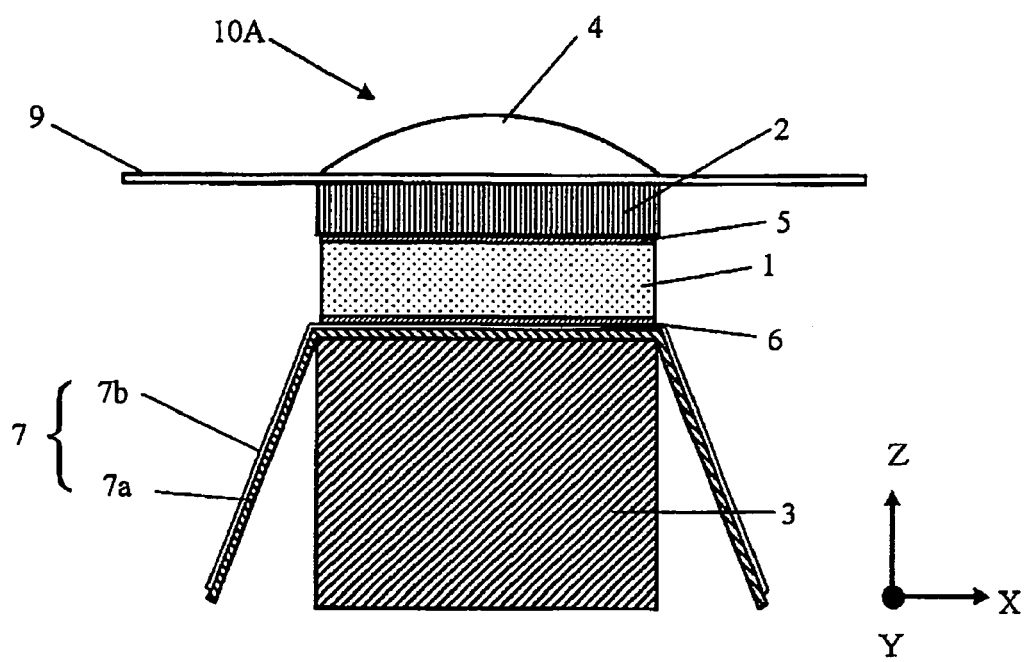
FIG. 1A is a cross-sectional view of a configuration of an ultrasound probe according to a first embodiment of the present invention.
Figure 1B:
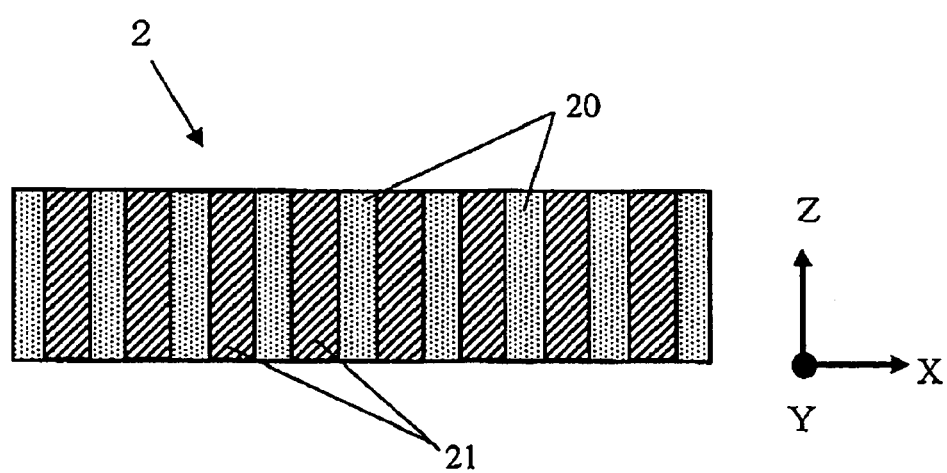
FIG. 1B is a cross-sectional view of a configuration example of an acoustic matching layer configuring the ultrasound probe shown in FIG. 1A.

FIG. 1A is a cross-sectional view of a configuration of an ultrasound probe according to a first embodiment of the present invention. FIG. 1B is a cross-sectional view of a configuration example of an acoustic matching layer configuring the ultrasound probe shown in FIG. 1A.

In FIG. 1A, an ultrasound probe 10A includes a plate-shaped piezoelectric element 1, an acoustic matching layer 2 laminated on a front surface (upper side in FIG. 1A) of the piezoelectric element 1, a backing material 3 mounted on a back surface (lower side in FIG. 1A) of the piezoelectric element 1 as required, and an acoustic lens 4 mounted on the front surface of the acoustic matching layer 2, also as required. Respective functions of these constituent elements are similar to the functions of the elements configuring a conventional ultrasound probe.

Among the constituent elements of the ultrasound probe 10A, the piezoelectric element 1 is made of a piezoelectric ceramic, such as a lead zirconate titanate (PZT) system, a piezoelectric monocrystal, such as a lead zinc niobate-lead titanate (PZN-PT) system or a lead magnesium niobate-lead titanate (PMN-PT) system, or a composite piezoelectric material that is a combination of the piezoelectric ceramic, the piezoelectric monocrystal, and a high-polymer material.

Alternatively, the piezoelectric element 1 is made of a piezoelectric material of a high-polymer material represented by PVDF, and the like. A ground electrode 5 is formed on the front surface of the piezoelectric element 1. A signal electrode 6 is formed on the back surface of the piezoelectric element 1. The ground electrode 5 and the signal electrode 6 are each formed by deposition of gold or silver, sputtering, or silver baking.

An electrical terminal 7 for signals is inserted between the signal electrode 6, formed on the piezoelectric element 1, and the backing material 3. In the electrical terminal 7 for signals, a conductive film 7b that is, for example, copper is deposited on one main surface of an insulating film 7a made of a high-polymer material such as polyimide. In this case, the one main surface of the insulating film 7a faces the piezoelectric element 1 side, such that the conductive film 7b of the electrical terminal 7 for signals is in contact with the signal electrode 6 formed on the piezoelectric element 1, and the insulating film 7a of the electrical terminal 7 for signals is in contact with the backing material 3. On the other hand, on the front surface of the ground electrode 5 formed on the piezoelectric element 1, the acoustic matching layer 2 made of a composite material including at least a conductive member, and an electrical terminal 9 for grounding are successively laminated. The electrical terminal 9 is a thin film made of metal, such as copper, and is conductive. In this case, the electrical terminal 9 for grounding is in contact with the conductive member in the composite material configuring the acoustic matching layer 2. The acoustic lens 4, for which a material such as silicon rubber is used, is mounted on the front surface of the electrical terminal 9 for grounding, as required. Any material that is electrically conductive can be used for the conductive film 7b and the electrical terminal 9 for grounding. The material is not limited to metal. In the electrical terminal 9 for grounding, the conductive film can be deposited on one main surface of an insulating film made of a high-polymer material, in a manner similar to the configuration of the electrical terminal 7 for signals. The conductive film can be laminated such as to be on the acoustic matching layer 2 side.

Operations of the ultrasound probe 10A configured as described above will be described.

The signal electrode 6 formed on the piezoelectric element 1 is electrically connected to one end of a cable (not shown), via the electrical terminal 7 for signals. The ground electrode 5 on the piezoelectric element 1 is also electrically connected to one end of a cable (not shown), via the conductive member in the composite material of the acoustic matching layer 2 and the electrical terminal 9 for grounding. The other end of each cable is connected to a main body section of an ultrasonic diagnostic apparatus (not shown). As a result, regular pulse voltage generated by the main body section of the ultrasonic diagnostic apparatus is applied to the piezoelectric element 1, and an ultrasonic wave is emitted. In addition, a received echo of an ultrasonic wave is converted to an electrical signal and transmitted to the main body section of the ultrasonic diagnostic apparatus.

As the acoustic matching layer 2 configured by the composite material including the conductive member, a material is selected such that the acoustic impedance of the acoustic matching layer 2 is between respective acoustic impedances of the piezoelectric element 1 and the subject (not shown) positioned on the acoustic lens 4 side. A configuration example of the composite material of the acoustic matching layer 2 including the conductive member is shown in FIG. 1B. In FIG. 1B, a direction in which the ultrasonic waves are emitted towards the subject is a Z direction. Two directions perpendicular to the Z direction are respectively an X direction and a Y direction.

In the acoustic matching layer 2 shown in FIG. 1B, conductive members 20 and, for example, insulating members or semiconductive members 21 serving as another member are alternately disposed in the X direction. A structure is formed in which, among these, a plurality of conductive members 20 are connected in two directions, the Y direction and the Z direction, and the insulating members or semiconductive members 21 are also similarly connected in the two directions, the Y direction and the Z direction. Here, the plurality of conductive members 20 provide a function for electrically connecting the ground electrode 5 of the piezoelectric element 1 and the electrical terminal 9 for grounding by respectively being in contact with the ground electrode 5 formed on the front surface of the piezoelectric element 1 and the electrical terminal 9 for grounding. Alternatively, the conductive members 20 can be arranged in a row in the Y direction in a state in which each end section faces the Z direction, and arranged in plural rows in the X direction. The insulating members or semiconductive members 21 surround the periphery of the conductive members 20. Among these, the conductive members 20 are connected in only one direction, the Z direction, and have no connection in the X direction or the Y direction. Similar effects can also be achieved by a structure in which the insulating members or semiconductive members 21 are connected in the three directions, the X direction, the Y direction, and the Z direction. Alternatively, similar effects can also be achieved by a structure in which the plurality of insulating members or semiconductive members 21 are arranged in a row in the Y direction in a state in which each end section faces the Z direction, and arranged in plural rows in the X direction. The conductive members 20 surround the periphery of the insulating members or semiconductive members 21. Among these, the conductive members 20 are connected in the three directions, the X direction, the Y direction, and the Z direction. The insulating members or semiconductive members 21 are connected in only one direction, the Z direction. Although the acoustic matching layer 2 is a composite of the conductive members 20 and the insulating members or semiconductive members 21, similar effects can also be achieved by a composite of other conductive members made of different materials.

As described above, the acoustic impedance of the acoustic matching layer 2 shown in FIG. 1A is required to be a value that is between the acoustic impedance of the piezoelectric element 1 and the acoustic impedance of the subject. For example, when a piezoelectric ceramic that is PZT-5H having an acoustic impedance value of about 30 MRayl is used as the piezoelectric element 1 and the subject is, for example, a living body having an acoustic impedance value of about 1.6 MRayl, a material having a value of about 6 to 8 MRayl is used because the acoustic matching layer 2 is a single layer.

A following configuration can be considered, the configuration described using, for example, the ultrasound probe 10A shown in FIG. 1A. In the configuration, an insulating member or a semiconductive member is used as the acoustic matching layer 2. A section of the piezoelectric element 1 corresponding to an end section of the ground electrode 5 is cut away, and an area (not shown) is formed in which the acoustic matching layer is not present. An electrical terminal (not shown) is taken out from this area. However, in a configuration such as this, although frequency band can be broadened in terms of performance, because the piezoelectric element 1 oscillates and generates the ultrasonic waves even in the area without the acoustic matching layer, the ultrasonic waves transmitted to the subject are distorted, and the ultrasonic image is degraded. Moreover, because the electrical terminal is taken out from the ground electrode 5 at only one location, when the piezoelectric element 1 breaks as a result of the ultrasound probe being dropped during operation or a mechanical impact, such as striking, being applied to the ultrasound probe, the ground electrode 5 may also similarly break and cause an electrical disconnection, or the like. As a result, malfunction may occur.

According to the first embodiment shown in FIG. 1A, a configuration is realized which solves these problems and in which the frequency band can be broadened. In other words, in the configuration, the ground electrode 5 of the piezoelectric element 1 is electrically connected with the electrical terminal 9 for grounding, via the plurality of conductive members 20 in the acoustic matching layer 2. Therefore, desired transmission and reception of ultrasonic waves can be uniformly performed over an entire surface of the piezoelectric element 1. Moreover, because the ground electrode 5 of the piezoelectric element 1 is connected with the electrical terminal 9 for grounding via the plurality of conductive members 20 in the acoustic matching layer 2, malfunction due to disconnection rarely occurs even when the piezoelectric element 1 and the ground electrode 5 break as a result of mechanical impact and the like.

Here, as an insulating member or semiconductive member 21 of the acoustic matching layer 2, a high-polymer material represented by, for example, epoxy resin, urethane resin, and polyimide, ceramics such as glass, crystallized glass, epoxy resin including a high concentration of tungsten powder, lead niobate ceramics, workable ceramics (free-cutting ceramics), monocrystal or polycrystal silicon, quartz crystal, and barium titanate, and the like are used. As the conductive member 20 of the acoustic matching layer 2, a metallic material, such as graphite, graphite filled with metal such as copper, copper, aluminum, silver, gold, and nickel, a high-polymer material in which, for example, metal such as gold, silver, copper, and aluminum, or carbon power is combined with a high-polymer compound such as epoxy resin and given conductivity, carbon, and the like are used. The conductive member 20 and the insulating member or semiconductive member 21 are not limited to the above-described materials. Other materials can be used as long as the materials have similar acoustic impedance as the above-described materials. The acoustic impedance of the composite material including the conductive member 20 and the insulating member or semiconductive member 21 is determined by respective volume amounts.

For example, when a value of 7 MRayl is to be obtained as a required acoustic impedance of the acoustic matching layer 2, a composite material can be formed in which graphite filled with copper having a value of about 10 MRayl is used as the conductive member 20, and epoxy resin having a value of about 3 MRayl is used as the insulating member 21. The volume amount of each member can be selected. In other words, when the volume amount of the epoxy resin is high, the acoustic impedance is closer to 3 MRayl. When the volume amount of the graphite filled with copper is high, the acoustic impedance is closer to 10 MRayl. Selection can be easily made to obtain the required 7 MRayl.

Here, a configuration of the composite material including the conductive member 20 and the insulating member or semiconductive member 21 is described. However, in addition to the configuration of the composite material combined as described above, for example, a configuration can be used in which a composite material including the conductive member is obtained by the conductive member being used in the insulating member or semiconductive member 21. In other words, the configuration is clearly not limited to that described above, as long as the composite material includes at least the conductive member 20 and provides a function for electrically connecting with an electrode surface of the piezoelectric element 1 and a function for allowing the acoustic impedance to be changed.

Here, the acoustic matching layer 2 is described as a single-layer type. However, similar effects can be achieved even in a configuration in which an acoustic matching layer including two or more layers is used, and even in a configuration in which the above-described composite material is used in each acoustic matching layer, or in some layers.

As described above, the acoustic matching layer can have the desired acoustic impedance by the composite material including at least the conductive member being provided as the acoustic matching layer provided on the subject side of the piezoelectric element. As a result, the frequency band can be broadened, thereby allowing a high-resolution, diagnostic image to be obtained. The electrical terminal can be connected at a plurality of areas of the piezoelectric element through the conductive members in the acoustic matching layer that is the composite material. Therefore, an ultrasound probe can be achieved that is highly reliable and has excellent operability.

According to the first embodiment, when the conductive members 20 and the insulating members or semiconductive members 21, shown in FIG. 1B, are formed having uniform widths in the Z direction is described. However, similar effects can be achieved in a configuration in which the width of the insulating members or semiconductive members 21 continuously change in the Z direction, forming a so-called wedge shape, or when the width changes in stages, and the acoustic impedance continuously changes or changes in stages in relation to the thickness in the Z direction.

According to the first embodiment, when the conductive members 20 and the insulating members or semiconductive members 21 in FIG. 1B are arrayed in an alternating manner at almost even intervals is described. However, similar effects can be achieved at random intervals or in a random array.

According to the first embodiment, a configuration is described in which, to exchange electrical signals with the ground electrode 5 of the piezoelectric element 1, the electrical terminal 9 for grounding is provided on the front surface of the acoustic matching layer 2, with the acoustic matching layer 2 between the electrical terminal 9 for grounding and the ground electrode 5. However, instead, similar effects can be achieved by a configuration in which the conductive member is formed on both surfaces or on one surface of the acoustic matching layer 2 in the Z direction by sputtering, plating, printing, or the like, and the electrical terminal 9 for grounding is connected to this area.

According to the first embodiment, as the acoustic matching layer 2, a coupled structure is used including the conductive member 20 and the insulating member or semiconductive member 21, each made of one type of material. However, similar effects can clearly be achieved even when at least one of the conductive member 20 and the insulating member or semiconductive member 21 is made of two types of materials or more. The structure is not limited to a coupled structure including one type of material for each member.

According to the first embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Second Embodiment>

Figure 2A:
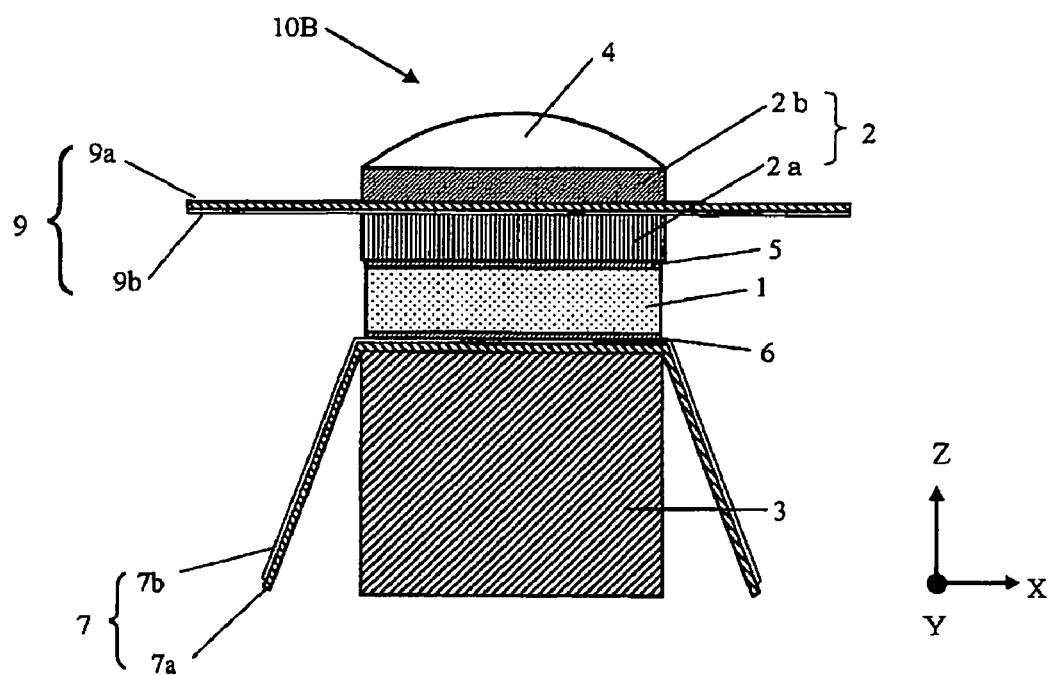
FIG. 2A is a cross-sectional view of a configuration of an ultrasound probe according to a second embodiment of the present invention.
Figure 2B:
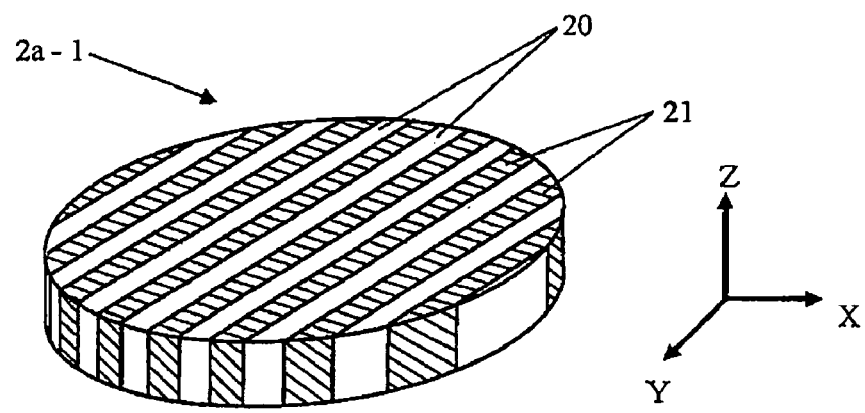
FIG. 2B is a perspective view of a configuration example of a first acoustic matching layer configuring the ultrasound probe shown in FIG. 2A.
Figure 2C:
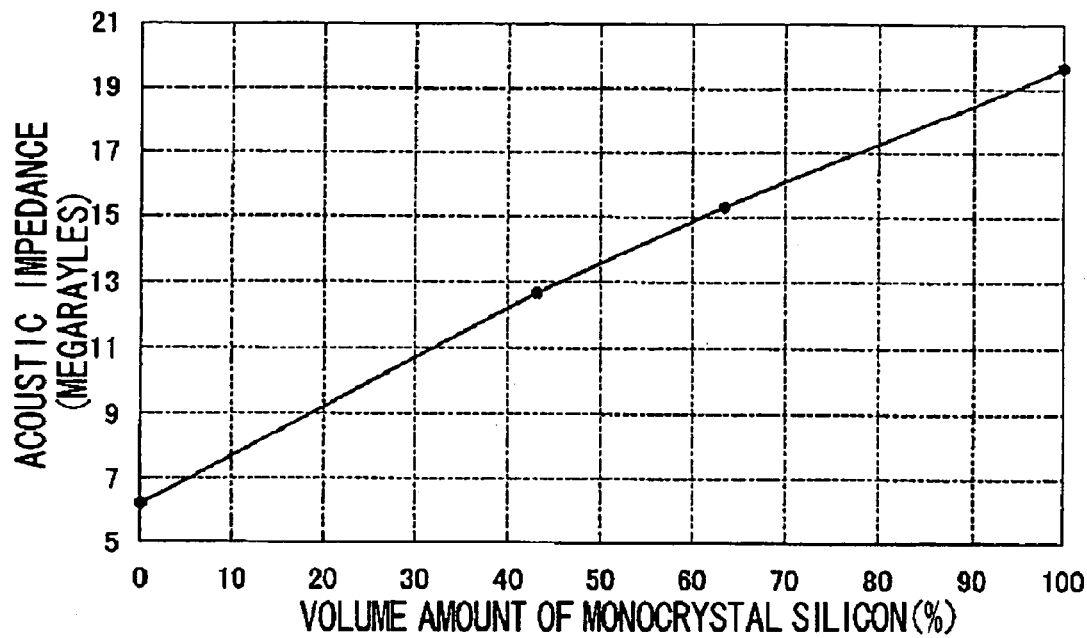
FIG. 2C is a graph showing a relationship between volume amounts of an insulating member or a conductive member in the first acoustic matching layer shown in FIG. 2B and acoustic impedance.
Figure 2D:
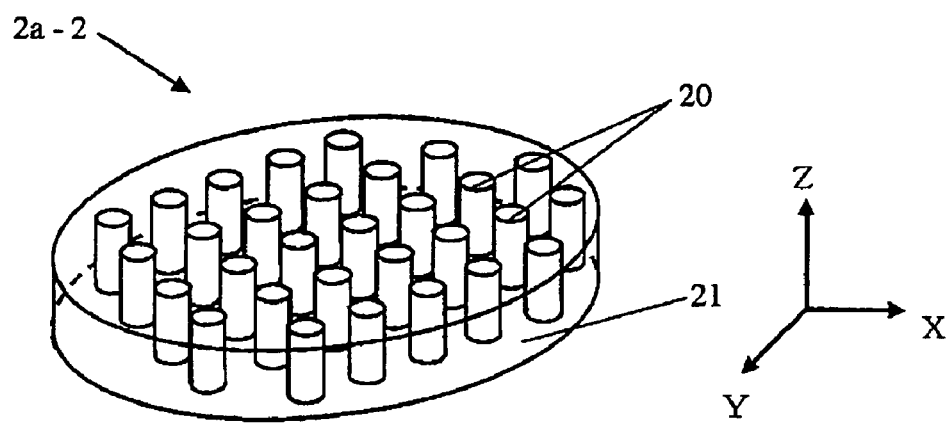
FIG. 2D is a perspective view of a configuration example of the first acoustic matching layer configuring the ultrasound probe shown in FIG. 2A.
Figure 2E:
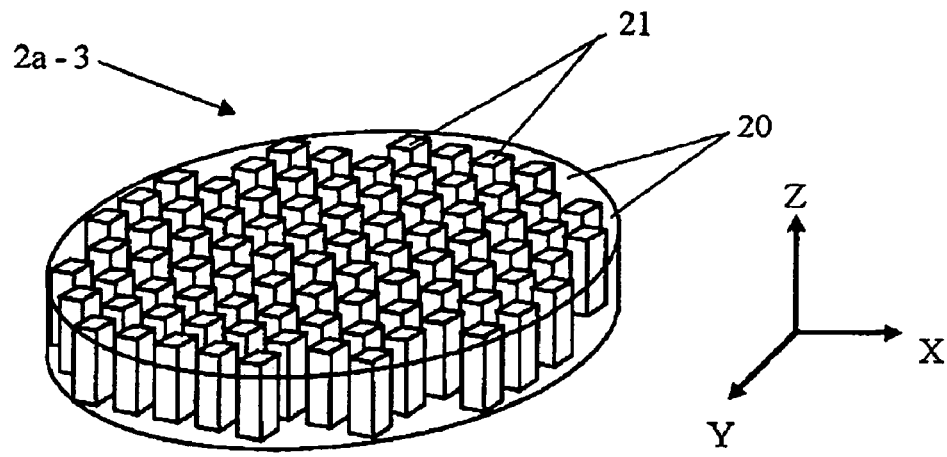
FIG. 2E is a perspective view of a configuration example of the first acoustic matching layer configuring the ultrasound probe shown in FIG. 2A.

FIG. 2A is a cross-sectional view of a configuration of an ultrasound probe according to a second embodiment of the present invention. FIG. 2B, FIG. 2D, and FIG. 2E are each perspective views of a configuration example of a first acoustic matching layer configuring the ultrasound probe shown in FIG. 2A. FIG. 2C is a graph of a relationship between volume amounts of a silicon monocrystal used as an insulating member or semiconductive member in the first matching layer shown in FIG. 2B and acoustic impedance.

In FIG. 2A, an ultrasound probe 10B includes the plate-shaped piezoelectric element 1, a two-layer acoustic matching layer 2 (2a and 2b) laminated on the front surface (upper side in FIG. 2A) of the piezoelectric element 1, the backing material 3 mounted on the back surface (lower side in FIG. 2A) of the piezoelectric element 1 as required, and the acoustic lens 4 mounted on the front surface of the acoustic matching layer 2 (2a and 2b), also as required. Respective functions of these constituent elements are similar to the functions of the elements configuring a conventional ultrasound probe.

Among the constituent elements of the ultrasound probe 10B, the piezoelectric element 1 is made of a piezoelectric ceramic, such as a PZT system, a piezoelectric monocrystal, such as a PZN-PT system or a PMN-PT system, or a composite piezoelectric material that is a combination of the piezoelectric ceramic, the piezoelectric monocrystal, and a high-polymer material. Alternatively, the piezoelectric element 1 is made of a piezoelectric material of a high-polymer material represented by PVDF, and the like. The ground electrode 5 is formed on the front surface of the piezoelectric element 1. The signal electrode 6 is formed on the back surface of the piezoelectric element 1. The ground electrode 5 and the signal electrode 6 are each formed by deposition of gold or silver, sputtering, or silver baking.

The electrical terminal 7 for signals is inserted between the signal electrode 6, formed on the piezoelectric element 1, and the backing material 3. In the electrical terminal 7 for signals, the conductive film 7b that is, for example, copper is deposited on one main surface of the insulating film 7a made of a high-polymer material such as polyimide. In this case, the one main surface of the insulating film 7a faces the piezoelectric element 1 side, such that the conductive film 7b of the electrical terminal 7 for signals is in contact with the signal electrode 6 formed on the piezoelectric element 1, and the insulating film 7a of the electrical terminal 7 for signals is in contact with the backing material 3. On the other hand, on the front surface of the ground electrode 5 formed on the piezoelectric element 1, a first acoustic matching layer 2a made of a composite material including an insulating member or semiconductive member and a conductive member, an electrical terminal 9 for grounding, and a second acoustic matching layer 2b made of a high-polymer material such as epoxy resin or polyimide are successively laminated. In the electrical terminal 9 for grounding, a conductive film (thickness is preferably 5 micrometers or less to minimize effect on characteristics) 9b that is, for example, copper is deposited on one main surface of an insulating film 9a made of a high-polymer material such as polyimide. In this case, the one main surface of the insulating film 9a faces the first acoustic matching layer 2a side, such that the conductive film 9b of the electrical terminal 9 for grounding is in contact with the conductive member in the composite material configuring the first acoustic matching layer 2a, and the second acoustic matching layer 2b is in contact with the insulating film 9a of the electrical terminal 9 for grounding. The second acoustic matching layer 2b can be an insulating member or a conductive member. The acoustic lens 4, for which a material such as silicon rubber is used, is mounted on the front surface of the second acoustic matching layer 2b, as required. Any material that is electrically conductive can be used for the conductive films 7b and 9b. The material is not limited to metal.

Operations of the ultrasound probe 10B configured as described above will be described.

The signal electrode 6 formed on the piezoelectric element 1 is electrically connected to one end of a cable (not shown), via the electrical terminal 7 for signals. The ground electrode 5 on the piezoelectric element 1 is also electrically connected to one end of a cable (not shown), via the conductive member in the composite material of the first acoustic matching layer 2a and the electrical terminal 9 for grounding. The other end of each cable is connected to a main body section of an ultrasonic diagnostic apparatus (not shown). As a result, regular pulse voltage generated by the main body section of the ultrasonic diagnostic apparatus is applied to the piezoelectric element 1, and an ultrasonic wave is emitted. In addition, a received echo of an ultrasonic wave is converted to an electrical signal and transmitted to the main body section of the ultrasonic diagnostic apparatus.

As the first acoustic matching layer 2a configured by the composite material including the insulating member or semiconductive member and the conductive member (referred to, hereinafter, as a composite material including the conductive member and the insulating member or semiconductive member), a material is selected such that the acoustic impedance of the first acoustic matching layer 2a is an intermediate value between respective acoustic impedances of the piezoelectric element 1 and the second acoustic matching layer 2b. A configuration example of each coupled structure formed by the conductive member and the insulating member or semiconductive member of the first acoustic matching layer 2a is shown in FIG. 2B, FIG. 2D, and FIG. 2E. In FIG. 2B, FIG. 2D, and FIG. 2E, a direction in which the ultrasonic waves are emitted towards the subject is a Z direction. Two directions perpendicular to the Z direction are respectively an X direction and a Y direction.

In a first acoustic matching layer 2a-1 shown in FIG. 2B, the conductive members 20 and the insulating members or semiconductive members 21 are each formed into a strip shape and alternately disposed in the X direction. A structure is formed in which, among these, the conductive members 20 are connected in two directions, the Y direction and the Z direction, and the insulating members or semiconductive members 21 are also similarly connected in the two directions, the Y direction and the Z direction. This structure is referred to as a 2-2 type coupled structure in the description below. Here, the plurality of conductive members 20 provide a function for electrically connecting the ground electrode 5 of the piezoelectric element 1 and the conductive film 9b of the electrical terminal 9 for grounding by respectively being in contact with the ground electrode 5 formed on the front surface of the piezoelectric element 1 and the conductive film 9b deposited on the one main surface of the insulating film 9a of the electrical terminal 9 for grounding.

In a first acoustic matching layer 2a-2 shown in FIG. 2D, a plurality of conductive members 20 are each formed into a columnar shape. The conductive members 20 are arranged in a row in the Y direction in a state in which each end section faces the Z direction, and arranged in plural rows in the X direction. The insulating member or semiconductive member 21 surrounds the periphery of the conductive members 20. Among these, the conductive members 20 are connected in only one direction, the Z direction, and have no connection in the X direction or the Y direction. The insulating member or semiconductive member 21 is a structure having a connection in three directions, the X direction, the Y direction, and the Z direction. This coupled structure is referred to as a 1-3 type coupled structure. Here, the plurality of conductive members 20 provide a function for electrically connecting the ground electrode 5 of the piezoelectric element 1 and the conductive film 9b of the electrical terminal 9 for grounding by respectively being in contact with the ground electrode 5 formed on the front surface of the piezoelectric element 1 and the conductive film 9b deposited on the one main surface of the insulating film 9a of the electrical terminal 9 for grounding.

In a first acoustic matching layer 2a-3 shown in FIG. 2E, a plurality of insulating members or semiconductive members 21 are each formed into a rectangular columnar shape. The insulating members or semiconductive members 21 are arranged in a row in the Y direction in a state in which each end section faces the Z direction, and arranged in plural rows in the X direction. The conductive member 20 surrounds the periphery of the insulating members or semiconductive members 21. A structure is formed in which, among these, the conductive members 20 are connected in three directions, the X direction, the Y direction, and the Z direction, and the insulating members or semiconductive members 21 are only connected in one direction, the Z direction. This structure is referred to as a 3-1 type coupled structure. Here, the conductive member 20 provides a function for electrically connecting the ground electrode 5 of the piezoelectric element 1 and the conductive film 9b of the electrical terminal 9 for grounding by respectively being in contact with the ground electrode 5 formed on the front surface of the piezoelectric element 1 and the conductive film 9b deposited on the one main surface of the insulating film 9a of the electrical terminal 9 for grounding.

As described above, the acoustic impedance of the first acoustic matching layer 2a shown in FIG. 2A is required to be a value that is between the acoustic impedance of the piezoelectric element 1 and the acoustic impedance of the second acoustic matching layer 2b. For example, when a piezoelectric ceramic that is PZT-5H having an acoustic impedance value of about 30 MRayl is used as the piezoelectric element 1 and the subject is, for example, a living body having an acoustic impedance value of about 1.6 MRayl, a material having an acoustic impedance value of about 3 MRayl is used as the second acoustic matching layer 2b. Therefore, a material that has an acoustic impedance value of at least 3 to 30 MRayl is required to be used as the first acoustic matching layer 2a.

In general, the acoustic impedance value of the first acoustic matching layer 2a is preferably between 5 to 20 MRayl. The band of a frequency characteristic tends to become broader as the value increases. Therefore, a material having a range of 10 to 20 MRayl is preferably used as the first acoustic matching layer 2a. Materials having an acoustic impedance value of 10 to 20 MRayl are, for example, glass, crystallized glass, epoxy resin including a high concentration of tungsten powder, lead niobate ceramics, workable ceramics (free-cutting ceramics), monocrystal or polycrystal silicon, and quartz crystal. However, all of these materials are electrically an insulating member or a semiconductive member.

A following configuration can be considered, the configuration described using, for example, the ultrasound probe 10B shown in FIG. 2A. In the configuration, an insulating member or a semiconductive member is used as the first acoustic matching layer 2a. A section of the piezoelectric element 1 corresponding to an end section of the ground electrode 5 is cut away, and an area (not shown) is formed in which the acoustic matching layer is not present. An electrical terminal (not shown) is taken out from this area. However, in a configuration such as this, although the frequency band can be broadened in terms of performance, because the piezoelectric element 1 oscillates and generates the ultrasonic waves even in the area without the acoustic matching layer, the ultrasonic waves transmitted to the subject are distorted, and the ultrasonic image is degraded. Moreover, because the electrical terminal is taken out from the ground electrode 5 at only one location, when the piezoelectric element 1 breaks as a result of the ultrasound probe being dropped during operation or a mechanical impact, such as striking, being applied to the ultrasound probe, the ground electrode 5 may also similarly break and cause an electrical disconnection, or the like. As a result, malfunction may occur.

According to the second embodiment shown in FIG. 2A, a configuration is realized which solves these problems and in which the frequency band can be broadened. In other words, in the configuration, the ground electrode 5 of the piezoelectric element 1 is electrically connected with the metal film 9b of the electrical terminal 9 for grounding, via the plurality of conductive members 20 in the first acoustic matching layer 2a. Therefore, desired transmission and reception of ultrasonic waves can be uniformly performed over an entire surface of the piezoelectric element 1. Moreover, because the ground electrode 5 of the piezoelectric element 1 is connected with the metal film 9b of the electrical terminal 9 for grounding via the plurality of conductive members 20 in the first acoustic matching layer 2a, malfunction due to disconnection rarely occurs even when the piezoelectric element 1 and the ground electrode 5 break as a result of mechanical impact and the like.

Here, as the insulating member or semiconductive member 21 in the first acoustic matching layers 2a-1, 2a-2, and 2a-3, ceramics such as above-mentioned glass, crystallized glass, epoxy resin including a high concentration of tungsten powder, lead niobate ceramics, workable ceramics (free-cutting ceramics), monocrystal or polycrystal silicon, quartz crystal, and barium titanate, and the like are used. As the conductive member 20 in the first acoustic matching layers 2a-1, 2a-2, and 2a-3, a metallic material, such as copper, aluminum, silver, gold, and nickel, a high-polymer material in which, for example, metal such as gold, silver, copper, and aluminum, or carbon power is combined with a high-polymer compound such as epoxy resin and given conductivity, graphite, carbon, and the like are used. The conductive member 20 and the insulating member or semiconductive member 21 are not limited to the above-described materials. Other materials can be used as long as the materials have similar acoustic impedance as the above-described materials. The acoustic impedance of the composite material including the conductive member 20 and the insulating member or semiconductive member 21 is determined by respective volume amounts.

Here, a configuration of the composite material including the conductive member 20 and the insulating member or semiconductive member 21 is described. However, in addition to the configuration of the composite material combined as described above, for example, a configuration can be used in which a composite material including the conductive member is obtained by the conductive member being used in the insulating member or semiconductive member 21. In other words, the configuration is clearly not limited to that described above, as long as the composite material includes at least the conductive member 20 and provides a function for electrically connecting with an electrode surface of the piezoelectric element 1 and a function for allowing the acoustic impedance to be changed.

In the 1-3 type, 2-2 type, and 3-1 type coupled structures, the composite material including the conductive member 20 and the insulating member or semiconductive member 21 has an acoustic impedance value that is between the acoustic impedances of each of the two types of materials. A material with a desired acoustic impedance can be obtained by the volume amounts of the conductive member 20 and the insulating member or semiconductive member 21 being changed.

To allow the composite material including the conductive member 20 and the insulating member or semiconductive member 21 and having the 1-3 type, 2-2 type, or 3-1 type coupled structure to function as the first acoustic matching layer 2a, the width and placement interval of the conductive members 20 are decided such that the composite material can integrally carry the ultrasonic waves. When the volume amount of the conductive material 20 is small, the width and placement interval are not required to be taken into consideration. The material for the conductive member 20 is selected, mainly focusing on the electrical connection function of the conductive member 20.

When the coupled structures shown in FIG. 2B, FIG. 2D, an FIG. 2E are used for the purpose of achieving the acoustic matching layer or, in other words, matching only the acoustic impedance with a desired value without requiring conductivity, the materials, namely the conductive member and the insulating member or semiconductive member, are not required to be selected. A coupled structure formed by insulating members, or a coupled structure formed by an insulating member, such as epoxy resin, and a semiconductive member, such as silicon, can be used.

Next, an example of a manufacturing method of the first matching layer 2a-1 having the 2-2 type coupled structure shown in FIG. 2B will be described below. Silicon monocrystal is used as the insulating member or semiconductive member 21. The silicon monocrystal is flat in the Z direction in FIG. 2B. Groove to be filled with the conductive member 20 are formed in the Y direction in FIG. 2B at an arbitrary interval on the planar surface by laser irradiation, chemical etching, machining, such as by a dicing machine, and the like. Next, the grooves are filled with a conductive adhesive, such as conductive epoxy resin including a powder, such as silver. The conductive adhesive is hardened. The conductive adhesive has a smaller acoustic impedance than the silicon monocrystal. Next, the silicon monocrystal is sliced to a thickness of about one-fourth wavelength in the Z direction, and the first acoustic matching layer 2a is formed. When a first acoustic matching layer 2a with an acoustic impedance that is similar to that of the silicon monocrystal is desired, the volume amount of the conductive adhesive serving as the conductive member 20 is reduced. When a small acoustic impedance value is required, the volume amount is increased.

For example, when Echobond 56C (Emerson and Cummings, Inc.) is used as the conductive adhesive for forming the conductive member 20 and silicon monocrystal is used as the insulating member or semiconductive member 21, respective acoustic impedances are about 6.5 MRayl and 19.7 MRayl. When the acoustic impedance (density×acoustic velocity) of the material formed by the silicon monocrystal being divided at arbitrary intervals and groove widths by a dicing machine and the grooves being filled with the Echobond 56C is measured, the acoustic impedance is 15.3 MRayl when the volume amount of the silicon monocrystal is 63.5%. The acoustic impedance is 12.7 MRayl when the volume amount of the silicon monocrystal is 43%.

FIG. 2C is a graph indicating a relationship between the volume amounts of the silicon monocrystal and the acoustic impedance created based on results of measurements taken for the two above-mentioned materials. As the graph clearly indicates, when the Echobond 56C is used as the conductive adhesive used to form the conductive member 20 and the volume amount of the silicon monocrystal is changed between a range of 0 percent (only the conductive adhesive) and 100 percent (only the silicon monocrystal), the acoustic impedance of the composite material including the conductive adhesive and the silicon monocrystal changes in an almost linear manner, from about 6.5 MRayl to 19.7 MRayl, which is the acoustic impedance of the silicon monocrystal. The inventors were able to confirm that a correlation is present between the volume amount and the acoustic impedance.

Next, another manufacturing method of the first matching layer 2a-1 having the 2-2 type coupled structure shown in FIG. 2B will be described below. A plate-shaped silicon monocrystal serving as the insulating member or semiconductive member 21 and a plate-shaped graphite or metal serving as the conductive member 20 are alternately laminated in the X direction in FIG. 2B and adhered. Alternatively, a thin metal film is respectively formed on one main surface of a plate-shaped silicon monocrystal, serving as the insulating member or semiconductive member 21, by a method such as sputtering, plating, or printing. Then, the silicon monocrystals on which the metal film is formed are successively laminated in the X direction in FIG. 2B and adhered. Subsequently, a slicing process is performed to obtain a desired thickness in the Z direction in FIG. 2B. Mass production becomes possible through use of this manufacturing method.

Next, a manufacturing method of the first matching layer 2a-2 having the 1-3 type coupled structure shown in FIG. 2D will be described below. Silicon monocrystal having a thickness in the Z direction in FIG. 2D is prepared as the insulating member or semiconductive member 21. Holes are formed in the silicon monocrystal by laser irradiation, chemical etching, machining, and the like, to provide a plurality of conductive members 20 at an arbitrary interval. Next, the holes are filled with a conductive adhesive, such as conductive epoxy resin including a powder, such as silver. The conductive adhesive is hardened. Then, the silicon monocrystal is processed into a thickness of about one-fourth wavelength, and the first acoustic matching layer is formed. When a first acoustic matching layer with an acoustic impedance that is similar to that of the silicon monocrystal is desired, the volume amount of the conductive adhesive that is the conductive member 21 is reduced. When a smaller acoustic impedance value is required, the volume amount of the conductive adhesive that is the conductive member 21 is increased.

The acoustic impedance of the silicon monocrystal is 19.7 MRayl, and the acoustic impedance of the Echobond 56C (Emerson and Cummings, Inc) serving as the conductive adhesive is about 6.5 MRayl. In a manner similar to the structure in FIG. 2B, the acoustic impedance can be a value between 6.5 MRayl and 19.7 MRayl through adjustment of respective volume amounts.

Next, a manufacturing method of the first matching layer 2a-3 having the 3-1 type coupled structure shown in FIG. 2E will be described below. Silicon monocrystal is prepared as the insulating member or semiconductive member 21. A plurality of grooves in the X direction and the Y direction are provided at an arbitrary interval in the silicon monocrystal by laser irradiation, chemical etching, machining, such as by using a dicing machine, and the like, and rectangular columns are formed. Then, the plurality of grooves are filled with the conductive member 20, such as conductive adhesive, and the conductive member 20 is hardened. The silicon monocrystal is then processed into a thickness of about one-fourth wavelength, and the first acoustic matching layer is formed.

As described above, the acoustic matching layer can have the desired acoustic impedance by the composite material including the conductive member and the insulating member or semiconductive member being provided as the acoustic matching layer provided on the subject side of the piezoelectric element. As a result, the frequency band can be broadened, thereby allowing a high-resolution, diagnostic image to be obtained. The electrical terminal can be connected at a plurality of areas of the piezoelectric element through the conductive members in the acoustic matching layer that is the composite material. Therefore, an ultrasound probe can be achieved that is highly reliable and has excellent operability.

According to the second embodiment, although a columnar shape is used for the conductive members 20 in the 1-3 type coupled structure shown in FIG. 2D, similar effects can be achieved even when other shapes, such as a rectangular column or a sphere, are used. Similar effects can also be achieved in a configuration in which a conical shape, such as a cone formed in the Z direction, is used and the acoustic impedance continuously changes in relation to the thickness in the Z direction.

According to the second embodiment, when the conductive members 20 and the insulating members or semiconductive members 21 in the 2-2 type coupled structure shown in FIG. 2B are formed with uniform widths in the Z direction is described. However, similar effects can be achieved in a configuration in which the insulating members or semiconductive members 21 continuously change in width in the Z direction, forming a so-called wedge shape, and the acoustic impedance continuously changes in relation to the thickness in the Z direction.

According to the second embodiment, when the conductive members 20 and the insulating members or semiconductive members 21 in the 2-2 type coupled structure shown in FIG. 2B, the 1-3 type coupled structure shown in FIG. 2D, and the 3-1 type coupled structure shown in FIG. 2E are arrayed in an alternating manner at almost even intervals is described. However, similar effects can be achieved at random intervals or in a random array.

According to the second embodiment, a configuration is described in which, to exchange electrical signals with the ground electrode 5 of the piezoelectric element 1, the electrical terminal 9 for grounding is provided on the front surface of the first acoustic matching layer 2a, with the first acoustic matching layer 2a between the electrical terminal 9 for grounding and the ground electrode 5. However, instead, similar effects can be achieved by a configuration in which the conductive member is formed on both surfaces or on one surface of the first acoustic matching layer 2a in the Z direction by sputtering, plating, printing, or the like, and the electrical terminal 9 for grounding is connected to this area.

According to the second embodiment, as the first acoustic matching layer 2a, a coupled structure is used including the conductive member 20 and the insulating member or semiconductive member 21, each of which is made of one type of material. However, similar effects can clearly be achieved even when at least one of the conductive member 20 and the insulating member or semiconductive member 21 is made of two types of materials or more. The structure is not limited to a coupled structure including one type of material for each member.

According to the second embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Third Embodiment>

Figure 3A:
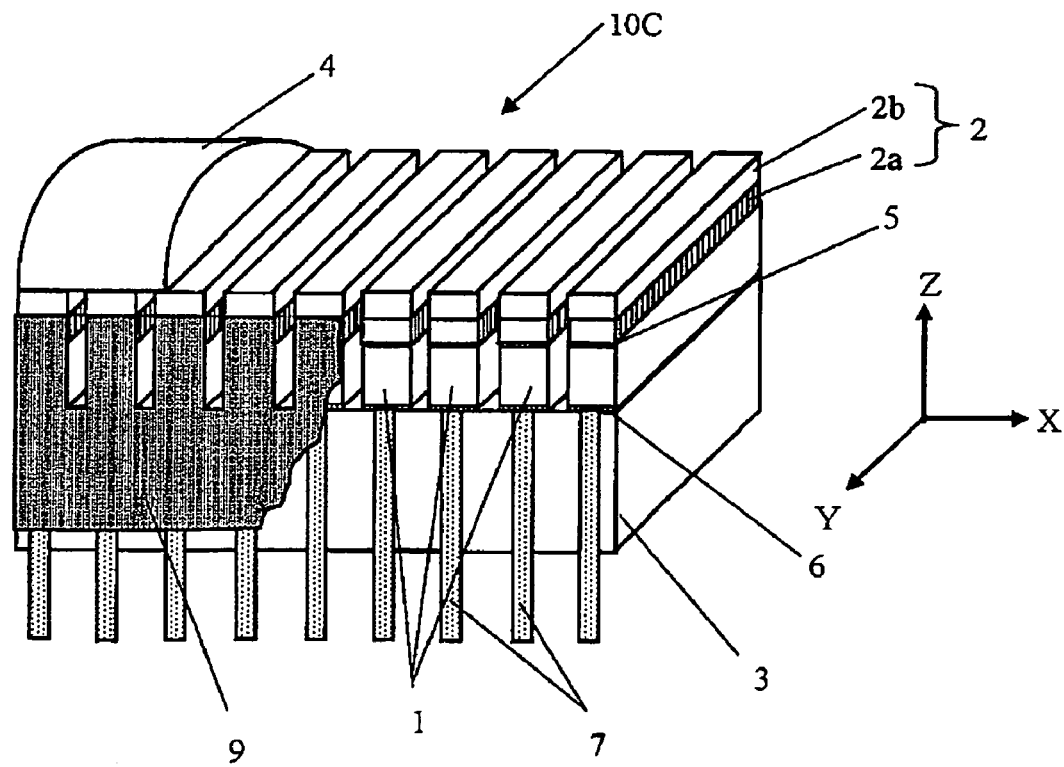
FIG. 3A is a perspective view of a configuration of an ultrasound probe according to a third embodiment of the present invention in which a portion thereof is a cutaway view.
Figure 3B:
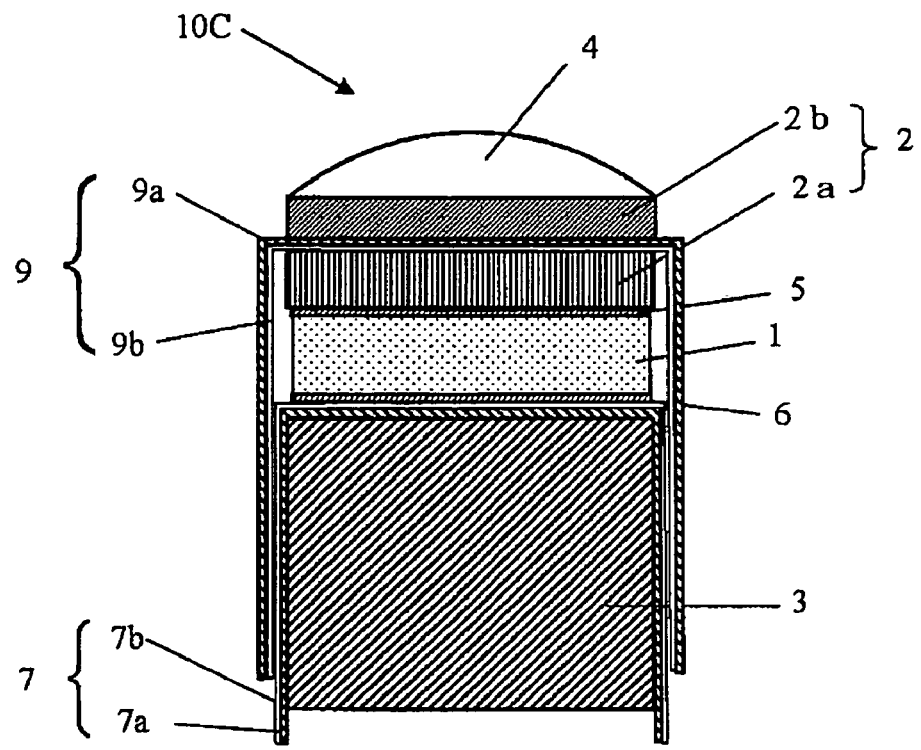
FIG. 3B is a cross-sectional view of the ultrasound probe shown in FIG. 3A.
Figure 3C:
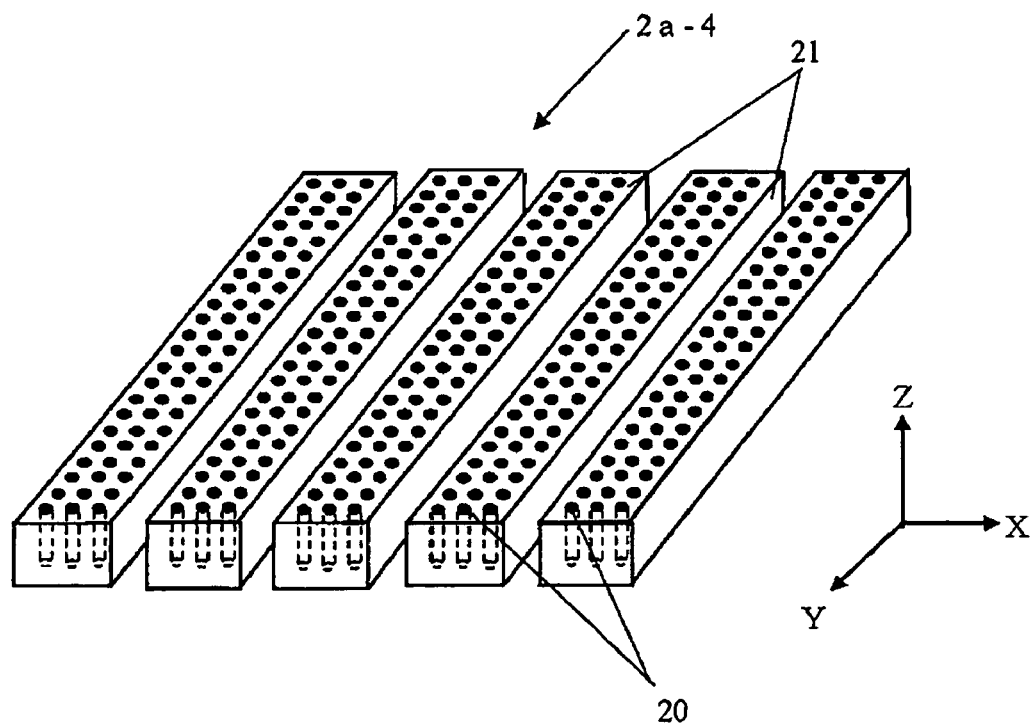
FIG. 3C is a perspective view of a detailed configuration example of elements configuring the ultrasound probe shown in FIG. 3A and FIG. 3B.
Figure 3D:
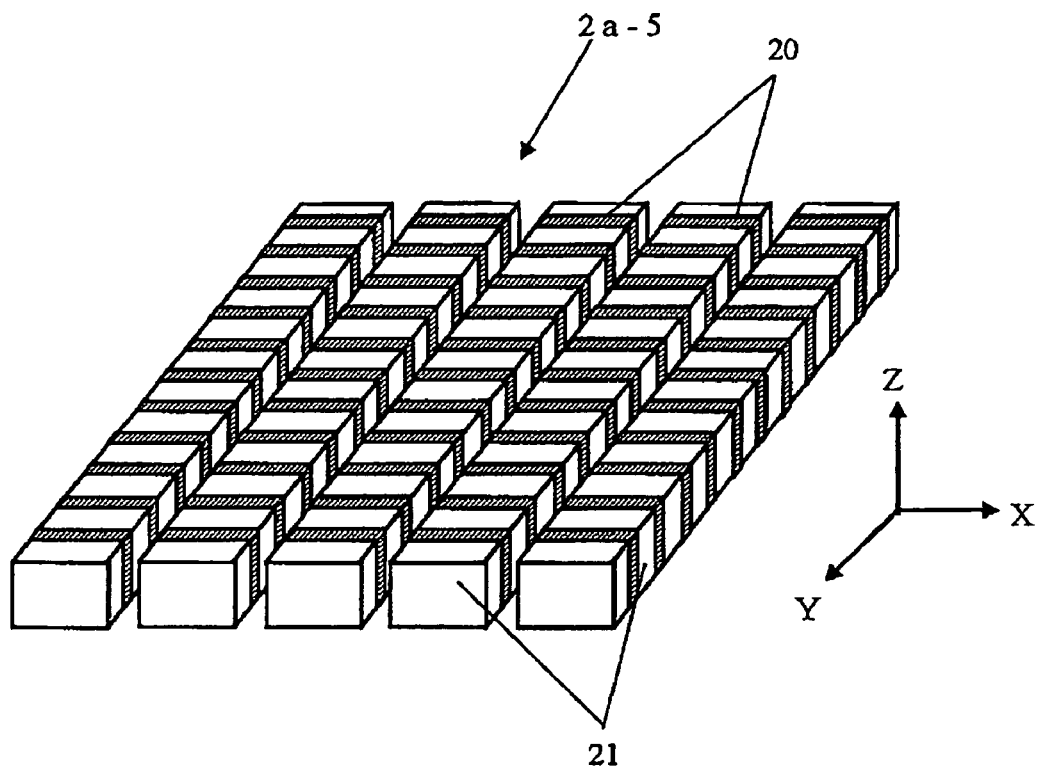
FIG. 3D is a perspective view of a detailed configuration example of elements configuring the ultrasound probe shown in FIG. 3A and FIG. 3B.

Next, a third embodiment of the present invention will be described. FIG. 3A is a perspective view of a configuration of an ultrasound probe according to a third embodiment of the present invention in which a portion thereof is a cutaway view. FIG. 3B is a cross-sectional view of the ultrasound probe shown in FIG. 3A in which a cross-section taken along a Y-Z plane, among three directions, X, Y, and Z, shown in FIG. 3A, is viewed from the X direction. FIG. 3C and FIG. 3D are each a perspective view of a detailed configuration example of elements configuring the ultrasound probe shown in FIG. 3A and FIG. 3B.

An ultrasound probe 10C shown in FIG. 3A and FIG. 3B include a plurality of piezoelectric elements 1 arrayed in the X direction, among X, Y, and Z shown in FIG. 3A, the two-layer acoustic matching layer 2 (2a and 2b) provided on the front surface in the Z direction that is the subject side, in correspondence with each piezoelectric element 1, the backing material 3 provided on the back surface of the piezoelectric elements 1 as required, the acoustic lens 4 provided in a shared manner on the plurality of acoustic matching layers 2 (2a and 2b), also as required, a plurality of electrical terminals 7 for signals inserted between the piezoelectric elements 1 and the backing material 3, and the electrical terminal 9 for grounding inserted between the first acoustic matching layer 2a and the second acoustic matching layer 2b. Respective functions of these constituent elements are similar to the functions of the elements configuring a conventional ultrasound probe.

To clarify the description, a manufacturing method of the ultrasound probe 10C shown in FIG. 3A and FIG. 3B will be described.

To form a plurality of piezoelectric elements 1, a plate material made of a piezoelectric ceramic, such as a PZT system, a piezoelectric monocrystal, such as a PZN-PT system or a PMN-PT system, a composite piezoelectric material that is a combination of the piezoelectric ceramic, the piezoelectric monocrystal, and a high-polymer material, a piezoelectric material of a high-polymer material represented by PVDF, and the like, and having a predetermined thickness is prepared. In other words, a piezoelectric plate material is prepared. The ground electrode 5 is formed on one main surface of the piezoelectric plate material, namely the front surface in the Z direction. The signal electrode 6 is formed on the back surface of the piezoelectric plate material. The ground electrode 5 and the signal electrode 6 are each formed by deposition of gold or silver, sputtering, or silver baking.

The plate-shaped backing material (a member replacing the backing material if the ultrasound probe does not include the backing material) 3 having a predetermined thickness is prepared. A plate material made of a composite material including a conductive member and an insulating member or semiconductive member, used to form a plurality of first acoustic matching layers 2a, is prepared. A plate material made of a high-polymer material, such as epoxy resin or polyamide, used to form a plurality of second acoustic matching layers 2b, is prepared. The plurality of electrical terminals 7 having an overall ribbon-like shape is prepared, in which a conductive film 7b made of copper or the like is deposited on one main surface of an insulating film 7a made of a high-polymer material such as polyimide. The electrical terminal 9 for grounding is prepared, in which a conductive film (thickness is preferably 5 micrometers or less to minimize effect on characteristics) 9b made of copper or the like is deposited on one main surface of an insulating film 9a, made of a high-polymer material such as polyimide. The high-polymer material, such as epoxy resin and polyimide, used to form the second acoustic matching layer 2b is an insulating member. However, a conductive member can be used instead. Any material that is electrically conductive can be used for the conductive films 7b and 9b. The material is not limited to metal.

As shown in FIG. 3A, the plurality of electrical terminals 7 for signals are placed on the front surface of the backing material 3 at a predetermined interval in the X direction. The piezoelectric plate material for forming the piezoelectric elements 1 is laminated on the plurality of electrical terminals 7 for signals. The plate material for forming the first acoustic matching layer 2a, the electrical terminal 9 for grounding, and the plate material for forming the second acoustic matching layer 2b are successively laminated on the front surface of the piezoelectric plate material. The laminate is integrally fixed. In this case, the one main surface of the insulating film 7a of the plurality of electrical terminals 7 for signals mounted between the backing material 3 and the piezoelectric plate material faces the piezoelectric plate material side (upper side in FIG. 3A), such that the conductive film 7b deposited on the one main surface of each insulating film 7a is in contact with the signal electrode 6 formed on the piezoelectric plate material and the insulating film 7a is in contact with the backing material 3. The one main surface of the insulating film 9a of the electrical terminal 9 for grounding mounted between the plate material for forming the first acoustic matching layers 2a and the plate material for forming the second acoustic matching layers 2b faces the first acoustic matching layer 2a side, such that the conductive film 9b formed on the one main surface of the insulating film 9a is in contact with the first acoustic matching layer 2a.

In this way, after the backing material 3, the plurality of electrical terminals 7 for signals, the piezoelectric plate material for forming the piezoelectric elements 1, the plate material for forming the first acoustic matching layers 2a, the electrical terminal 9 for grounding, and the plate material for forming the second acoustic matching layers 2b are integrally fixed, a slicing machine or the like is used to form a plurality of grooves having a depth from the front surface of the second acoustic matching layer 2b to the front surface section of the backing material 3. In other words, division grooves are formed that divide the laminate into a plurality of piezoelectric element units, a single unit including the second acoustic matching layer 2b, the electrical terminal 9 for grounding, the first acoustic matching layer 2a, the piezoelectric plate material, the electrical terminal 7 for signals, and a portion of the backing material 3. In this case, the division grooves are formed in intermediate sections between the electrical terminals 7 for signals disposed at a predetermined interval in the X direction. As a result, a piezoelectric element row in which the piezoelectric element units are arrayed in parallel is formed. Next, each division groove is filled with a material (not shown), such as silicone rubber or urethane rubber, that has low acoustic coupling. Furthermore, the acoustic lens 4, using a material such as silicone rubber, is mounted on the upper surface of the second acoustic matching layers 2b, as required. In an ultrasound probe that does not include the backing material, the member replacing the backing material 3 is removed at this stage.

Here, a configuration is described in which the electrical terminal 9 for grounding and the ground electrode 5 formed on the piezoelectric element 1 are electrically connected as a result of the electrical terminal 9 for grounding, in which the conductive film 9b is deposited on the insulating film 9a, being inserted between the first acoustic matching layer 2a and the second acoustic matching layer 2b, and the conductive film 9b of the electrical terminal 9 for grounding and the conductive member of the first acoustic matching layer 2a coming into contact. However, similar operations can also be performed by a conductive member being used as the second acoustic matching layer 2b, the electrical terminal 9 for grounding on which the conductive film 9b is deposited being mounted on the front surface of the second acoustic matching layer 2b, and the electrical terminal 9 for grounding and the ground electrode 5 formed on the piezoelectric element 1 being electrically connected, via the first acoustic matching layer 2a and the second acoustic matching layer 2b.

Operations of the ultrasound probe 10C configured as described above will be described below.

The signal electrode 6 formed on the back surface of the piezoelectric element 1 is electrically connected to one end of a cable (not shown), via the electrical terminal 7 for signals. The ground electrode 5 formed on the front surface of the piezoelectric element 1 is also electrically connected to one end of a cable (not shown), via the conductive member in the composite material of the first acoustic matching layer 2a and the electrical terminal 9 for grounding. The other end of each cable is connected to a main body section of an ultrasonic diagnostic apparatus (not shown). As a result, regular pulse voltage generated by the main body section of the ultrasonic diagnostic apparatus is applied to the piezoelectric element 1, and an ultrasonic wave is emitted. In addition, a received echo of an ultrasonic wave is converted to an electrical signal and transmitted to the main body section of the ultrasonic diagnostic apparatus.

In this case, the conductive member of the first acoustic matching layer 2a, details of which will be described hereafter, is merely required to have a shape that electrically connects the ground electrode 5 formed on the piezoelectric element 1 and the conductive film 9b of the electrical terminal 9 for grounding. The conductive member is not limited to a particular shape. A configuration is preferred in which the conductive member of the first acoustic matching layer 2a allows the ground electrode 5 of the piezoelectric element 1 and the conductive film 9b of the electrical terminal 9 for grounding to be electrically connected at two or more areas of a single piezoelectric element 1. When the number of conductive members 20 is large, malfunction caused by disconnection of a signal transmission line becomes infrequent, even when both the ground electrode 5 and the piezoelectric element 1 are broken. High reliability is achieved. Moreover, a main purpose of the insulating member or semiconductive member in the first acoustic matching layer 2a is to select the acoustic impedance. Therefore, when the two-layer acoustic matching layer is provided as according to the third embodiment, the acoustic impedance of the first acoustic matching layer 2a is required to be a value between the acoustic impedance of the piezoelectric element 1 and the acoustic impedance of the second acoustic matching layer 2b. For example, a value within a range of 5 MRayl to 15 MRayl is selected. A material allowing an acoustic impedance of a range such as this to be obtained serves as the material that is a composite of the conductive member and the insulating member or semiconductive member.

An example of each coupled structure formed by the conductive member and the insulating member or semiconductive member in the first acoustic matching layer 2a configured by the composite material including the conductive member and the insulating member or semiconductive member is shown in FIG. 3C and FIG. 3D. In FIG. 3C and FIG. 3D, the Z direction that is the thickness direction indicates a direction towards the subject side. The X direction indicates a direction in which the piezoelectric elements 1 are arrayed. The Y direction indicates a direction perpendicular to the X direction and the Z direction.

In FIG. 3C, the plurality of conductive members 20 forming a first acoustic matching layer 2a-4 are formed having a cylindrical shape, in which axial centers are aligned in the Z direction. The conductive members 20 are connected in only one direction, the Z direction. The insulating member or semiconductive member 21 form a structure that is connected in three directions, the X direction, the Y direction, and the Z direction. The coupled structure of the composite material including the conductive members 20 and the insulating member or semiconductive member 21 is referred to as a 1-3 type coupled structure. A total of 66 conductive members 20 of a single first acoustic matching layer 2a-4 corresponding to a piezoelectric unit, namely a single piezoelectric element 1, are disposed in 3×22 rows. As described above, regarding the number of conductive members 20, reliability increases as the connection areas with the ground electrode 5 of the piezoelectric element 1 increase. However, regarding the number of conductive members 20, two conductive members 20 or more is merely required. The number is not limited to 66 conductive members 20. However, a configuration is required that allows the conductive members 20 to function as the first acoustic matching layer 2a or, in other words, allows the composite material including the conductive members 20 and the insulating member or semiconductive member 21 to acoustically function as a single acoustic matching layer. The first acoustic matching layer 2a-4 shown in FIG. 3C is shown in a state in which the first acoustic matching layer 2a-4 is already divided in correspondence to the piezoelectric elements 1. However, in a state before division, the overall first acoustic matching layer 2a-4 is a single plate, as described above. On the other hand, when the conductive members 20 are not required have an acoustic matching function or, in other words, the volume amount of the conductive members 20 is significantly smaller than that of the insulating member or semiconductive member 21, similar effects can be achieved by the conductive members 20 merely providing a function for allowing connection to the ground electrode 5 of the piezoelectric element 1.

In this way, the plurality of conductive members 20 are respectively in contact with the ground electrode 5 of the piezoelectric element 1 and the metal film 9b of the electrical terminal 9 for grounding, and provide a function for electrically connecting the ground electrode 5 and the metal film 9b in the Z direction that is the thickness direction. Here, a material having a connection in one direction, the Z direction, serves as the conductive members 20. A material having a connection in three directions, the X direction, the Y direction, and the Z direction, serves as the insulating member or semiconductive member 21. However, these materials can be interchanged. Similar effects can be achieved in a coupled structure in which the insulating member or semiconductive member side has a connection in one direction, the Z direction, and the conductive member side has a connection in three directions, the X direction, the Y direction, and the Z direction, namely a 3-1 type coupled structure (not shown).

In an acoustic matching layer 2a-5 shown in FIG. 3D, the conductive members 20 and the insulating members or semiconductive members 21 are alternately disposed. The conductive members 20 are connected in two directions, the X direction that is the direction in which the piezoelectric elements 1 are arrayed and the Z direction that is the thickness direction. The insulating members or semiconductive members 21 are similarly connected in two directions, the X direction that is the direction in which the piezoelectric elements 1 are arrayed and the Z direction. The coupled structure of the composite material including the conductive members 20 and the insulating members or semiconductive members 21 is referred to as a 2-2 type coupled structure. Therefore, the plurality of conductive members 20 allows electrical connection in the Z direction that is the thickness direction, between the ground electrode 5 of the piezoelectric element 1 and the conductive member of the electrical terminal 9 for grounding.

In FIG. 3D, 11 conductive members 20 of a single first acoustic matching layer 2a-5 corresponding to a single piezoelectric element 1 are disposed in the Y direction alternately with the insulating members or semiconductive members 21. As described above, reliability increases as the connection areas with the ground electrode 5 of the piezoelectric element 1 increase. However, regarding the number of conductive members 20, two conductive members 20 or more are merely required. However, a configuration is required that allows the conductive members 20 to function as the first acoustic matching layer 2a or, in other words, allows the composite material including the conductive members 20 and the insulating members or semiconductive members 21 to function as a single acoustic matching layer. The first acoustic matching layer 2a-5 shown in FIG. 3D is shown in a state in which the first acoustic matching layer 2a-5 is already divided in correspondence to the piezoelectric elements 1. However, in a state before division, the overall first acoustic matching layer 2a-4 is a single plate, as described above. A configuration is formed in which the conductive members 20 and the insulating members or semiconductive members 21 are connected in the X direction that is the direction in which the piezoelectric elements 1 are arrayed. On the other hand, when the conductive members 20 are not required have an acoustic matching function or, in other words, the volume amount of the conductive members 20 is significantly smaller than that of the insulating members or semiconductive members 21, similar effects can be achieved by the conductive members 20 merely providing a function for allowing connection to the ground electrode 5 of the piezoelectric element 1.

In FIG. 3D, the 2-2 type coupled structure is shown in which the conductive members 20 and the insulating members or semiconductive members 21 of the first acoustic matching layer 2a-5 are configured roughly parallel with the direction in which the piezoelectric elements 1 are arrayed. However, similar effects can also be achieved in a 2-2 type coupled structure in which the conductive members 20 and the insulating members or semiconductive members 21 are arrayed in a direction perpendicular to the direction in which the piezoelectric elements 1 are arrayed, or in another direction.

As described above, in the first acoustic matching layers 2a-4 and 2a-5 having the coupled structures shown in FIG. 3C and FIG. 3D, the acoustic impedance is required to be a value that is between the acoustic impedance of the piezoelectric element 1 and the acoustic impedance of the second acoustic matching layer 2b. However, when the acoustic matching layer is a two-layer type as according to the third embodiment, for example, when a PZT-5H piezoelectric ceramic having an acoustic impedance value of about 30 MRayl is used as the piezoelectric element 1 and the subject is, for example, a living body having an acoustic impedance value of about 1.6 MRayl, a material having an acoustic impedance value of about 3 MRayl is used for the second acoustic matching layer 2b.

Therefore, a material having an acoustic impedance value that is at least between 3 to 30 MRayl is required for the first acoustic impedance matching layer 2a. In general, the acoustic impedance of the first acoustic matching layer 2a is preferably a value between 5 to 20 MRayl. The band of the frequency characteristic tends to become broader as the value increases. Therefore, to achieve a frequency characteristic of a broad band, the acoustic impedance value of the first acoustic matching layer 2a is required to be large. A material having an acoustic impedance within a range of 10 to 20 MRayl is used.

However, materials having an acoustic impedance value within this range are, for example, glass, crystallized glass, epoxy resin including a high concentration of tungsten powder, lead niobate ceramics, workable ceramics (free-cutting ceramics), monocrystal or polycrystal silicon, and quartz crystal. However, all of these materials are electrically an insulating member or a semiconductive member.

A following configuration can be considered, the configuration described using, for example, the ultrasound probe 10C shown in FIG. 3B. In the configuration, a section of the piezoelectric element 1 corresponding to an end section of the ground electrode 5 is cut away, and an area (not shown) is formed in which the acoustic matching layer is not present. An electrical terminal (not shown) is taken out from this area. However, in a configuration such as this, although the frequency band can be broadened in terms of performance, because the piezoelectric element 1 oscillates and generates the ultrasonic waves even in the area without the acoustic matching layer, the ultrasonic waves transmitted to the subject are distorted, and the ultrasonic image is degraded. Moreover, because the electrical terminal is taken out from the ground electrode 5 at only one location, when the piezoelectric element 1 breaks as a result of the ultrasound probe being dropped during operation or a mechanical impact, such as striking, being applied to the ultrasound probe, the ground electrode 5 may also similarly break and cause an electrical disconnection, or the like. As a result, malfunction may occur.

According to the third embodiment, a configuration is realized which solves these problems and in which the frequency band can be broadened. In other words, in the configuration, the ground electrode 5 of the piezoelectric element 1 is electrically connected with the metal film 9b of the electrical terminal 9 for grounding, via the plurality of conductive members 20 in the first acoustic matching layer 2a. Therefore, desired transmission and reception of ultrasonic waves can be uniformly performed over an entire surface of the piezoelectric element 1 because the acoustic matching layer is provided over the entire surface of the piezoelectric element 1. Moreover, because the ground electrode 5 of the piezoelectric element 1 is connected with the metal film 9b of the electrical terminal 9 for grounding via the plurality of conductive members 20 in the first acoustic matching layer 2a, malfunction due to disconnection rarely occurs even when the piezoelectric element 1 and the ground electrode 5 break as a result of mechanical impact and the like.

On the other hand, as the insulating members or semiconductive members 21 of the first acoustic matching layers 2a-3 and 2a-4, ceramics such as glass, crystallized glass, epoxy resin including a high concentration of tungsten powder, lead niobate ceramics, workable ceramics (free-cutting ceramics), monocrystal or polycrystal silicon, quartz crystal, and barium titanate, and the like that are materials used according to the second embodiment are used. As the conductive members 20 of the first acoustic matching layers 2a-3 and 2a-4, a metal, such as copper, aluminum, silver, gold, and nickel, a high-polymer material in which, for example, metal such as gold, silver, copper, and aluminum, or carbon power is combined with a high-polymer compound such as epoxy resin and given conductivity, graphite, carbon, and the like are used. The acoustic impedances of the composite materials having the 1-3 type coupled structure, the 2-2 type coupled structure, and the 3-1 type coupled structure, including the conductive members 20 and the insulating members or semiconductive members 21, are determined by respective volume amounts. For example, when silver is used as the conductive member 20 and an X-cut quartz crystal is used as the insulating member, the respective acoustic impedances of each individual material are 38 MRayl and 15.3 MRayl. A desired value between the acoustic impedance of 38 MRayl of the X-cut quartz crystal and the acoustic impedance of 15.3 MRayl of silver can be obtained in a manner similar to the graph in FIG. 2C according to the second embodiment, as a result of the volume amounts of the two types of materials being changed.

The conductive member 20 and the insulating member or semiconductive member 21 can be materials other than those described above, as long as the material can achieve the objects of the present invention. The materials are not limited to those described above. According to the third embodiment, a first acoustic matching layer 2a having a coupled structure including one type of conductive member 20 and one type of the insulating member or semiconductive member 21 is described. However, similar effects can clearly be achieved even when two or more types of materials are used, such as two types of conductive members and one to three types of insulating members. The structure is not limited to a coupled structure including one type of material for each member.

To allow the composite material including the conductive member 20 and the insulating member or semiconductive member 21 and having the 1-3 type, 2-2 type, or 3-1 type coupled structure to function as the first acoustic matching layer 2a, the width and placement interval of the conductive members 20 are decided such that the composite material can integrally carry the ultrasonic waves. When the volume amount of the conductive material 20 is small, the width and placement interval are not required to be taken into consideration. The material of the conductive member 20 is selected, mainly focusing on the electrical connection function of the conductive member 20.

As a manufacturing method of the first acoustic matching layer 2a-4 having the 1-3 type coupled structure shown in FIG. 3C, the first acoustic matching layer 2a-4 is merely required to be manufactured by a method similar to that used to form the first acoustic matching layer 2a-2 shown in FIG. 2D, according to the second embodiment. As a manufacturing method of the first acoustic matching layer 2a-4 having the 2-2 type coupled structure shown in FIG. 3D, the first acoustic matching layer 2a-4 is merely required to be manufactured by a method similar to that used to form the first acoustic matching layer 2a-1 shown in FIG. 2B, according to the second embodiment.

As described above, the acoustic matching layer can have the desired acoustic impedance by the composite material including the conductive member and the insulating member or semiconductive member being provided as the acoustic matching layer provided on the subject side of the piezoelectric element. As a result, the frequency band can be broadened, thereby allowing a high-resolution, diagnostic image to be obtained. Moreover, because the electrical terminal can be taken out from the conductive member configuring the composite material, an ultrasound probe can be achieved that is highly reliable and has excellent operability.

According to the third embodiment, although a columnar shape is used for the conductive members 20 in the 1-3 type coupled structure, similar effects can be achieved even when other shapes, such as a rectangular column or a sphere, are used. Similar effects can also be achieved in a configuration in which a conical shape, such as a cone formed in the Z direction, is used for the conductive members 20 in the 1-3 type coupled structure, and the acoustic impedance continuously changes in relation to the thickness in the Z direction.

According to the third embodiment, when the conductive members 20 and the insulating members or semiconductive members 21 in the 2-2 type coupled structure are formed with uniform widths in the Z direction is described. However, similar effects can be achieved in a configuration in which the members continuously change in width in the Z direction, forming a so-called wedge shape, and the acoustic impedance continuously changes in relation to the thickness in the Z direction.

According to the third embodiment, when the conductive members 20 and the insulating members or semiconductive members 21 in the 1-3 type coupled structure, the 2-2 type coupled structure, and the 3-1 type coupled structure are arrayed in an alternating manner at almost even intervals is described. However, similar effects can be achieved at random intervals or in a random array.

According to the third embodiment, a configuration is described in which, to exchange electrical signals with the ground electrode 5 of the piezoelectric element 1, the electrical terminal 9 for grounding is provided on the front surface of the first acoustic matching layer 2a, with the first acoustic matching layer 2a between the electrical terminal 9 for grounding and the ground electrode 5. However, instead, similar effects can be achieved by a configuration in which the conductive member is formed on both surfaces or on one surface of the first acoustic matching layer 2a in the Z direction by sputtering, plating, printing, or the like, and the electrical terminal 9 for grounding is connected to this area.

According to the third embodiment, a configuration in which the plurality of piezoelectric elements 1 are arrayed in a one-dimensional manner is described. However, similar effects can also be achieved in a configuration that is a so-called two-dimensional array, in which the plurality of piezoelectric elements 1 are arrayed in a two-dimensional manner.

According to the third embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Fourth Embodiment>

Figure 4A:
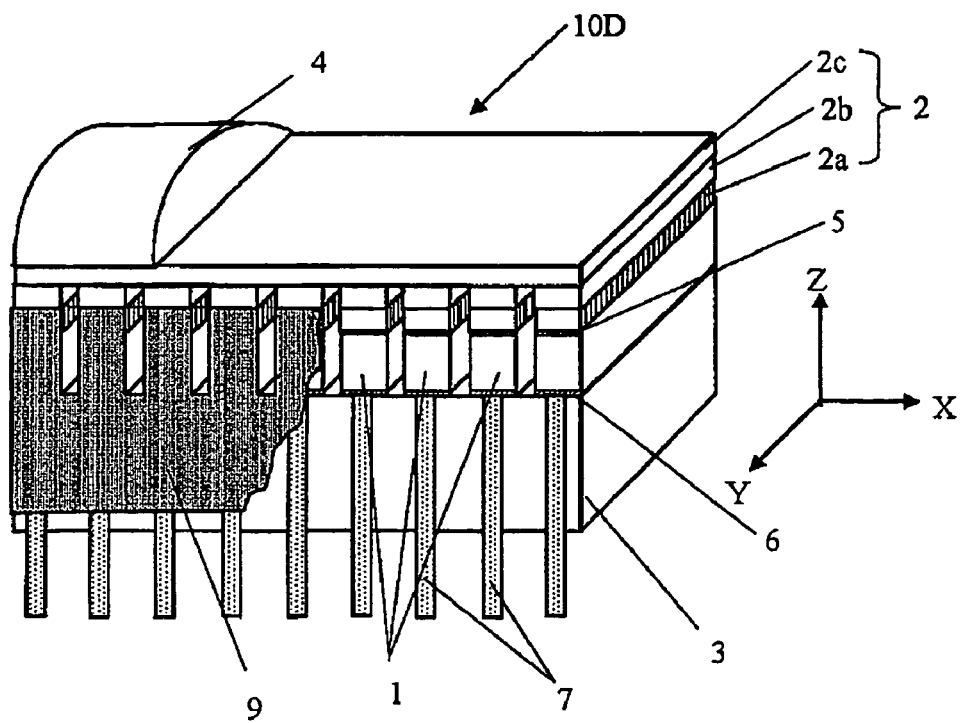
FIG. 4A is a perspective view of a configuration of an ultrasound probe according to a fourth embodiment of the present invention in which a portion thereof is a cutaway view.
Figure 4B:
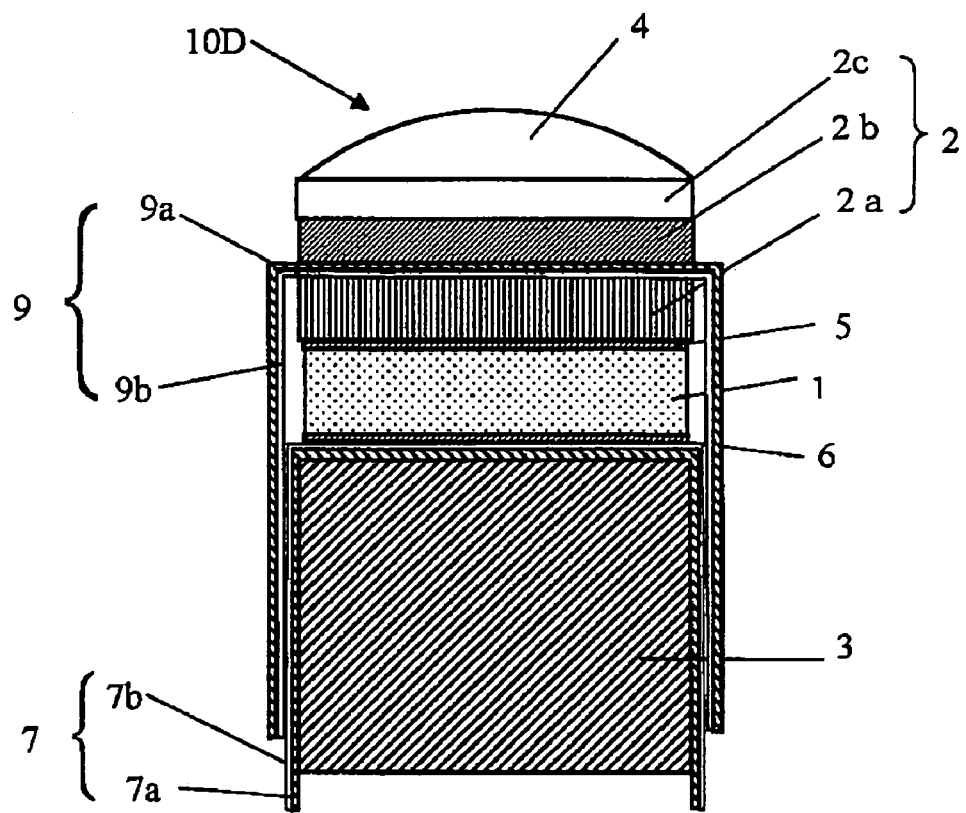
FIG. 4B is a cross-sectional view of the ultrasound probe shown in FIG. 4A.

Next, a fourth embodiment of the present invention will be described. FIG. 4A is a perspective view of a configuration of an ultrasound probe according to the fourth embodiment of the present invention in which a portion thereof is a cutaway view. FIG. 4B is a cross-sectional view of the ultrasound probe shown in FIG. 4A in which a cross-section taken along a Y-Z plane, among three directions, X, Y, and Z, shown in FIG. 4A, is viewed from the X direction.

An ultrasound probe 10D shown in FIG. 4A and FIG. 4B include the plurality of piezoelectric elements 1 arrayed in the X direction, among X, Y, and Z shown in FIG. 4A, the acoustic matching layer 2 including a plurality of first acoustic matching layers 2a laminated on the front surface in the Z direction that is the subject side in correspondence with each piezoelectric element 1, a plurality of second acoustic matching layers 2b, and a third acoustic matching layer 2c laminated on the second acoustic matching layers 2b in a shared manner, the backing material 3 provided on the back surface of the piezoelectric elements 1 as required, the acoustic lens 4 provided on the front surface of the acoustic matching layer 2, also as required, the plurality of electrical terminals 7 for signals inserted between the piezoelectric elements 1 and the backing material 3, and the electrical terminal 9 for grounding inserted between the first acoustic matching layer 2a and the second acoustic matching layer 2b. Respective functions of these constituent elements are similar to the functions of the elements configuring a conventional ultrasound probe.

To clarify the description, a manufacturing method of the ultrasound probe 10D shown in FIG. 4A and FIG. 4B will be described.

To form the plurality of piezoelectric elements 1, a plate material made of a piezoelectric ceramic, such as a PZT system, a piezoelectric monocrystal, such as a PZN-PT system or a PMN-PT system, a composite piezoelectric material that is a combination of the piezoelectric ceramic, the piezoelectric monocrystal, and a high-polymer material, a piezoelectric material of a high-polymer material represented by PVDF, and the like and having a predetermined thickness is prepared. In other words, a piezoelectric plate material is prepared. The ground electrode 5 is formed on one main surface of the piezoelectric plate material, namely the front surface in the Z direction. The signal electrode 6 is formed on the back surface of the piezoelectric plate material. The ground electrode 5 and the signal electrode 6 are each formed by deposition of gold or silver, sputtering, or silver baking.

The plate-shaped backing material (a member replacing the backing material when the ultrasound probe does not include the back-surface load material) 3 having a predetermined thickness is prepared. A plate material made of a composite material including a conductive member and an insulating member or semiconductive member, used to form the plurality of first acoustic matching layers 2a, is prepared. A plate material made of a high-polymer material, such as epoxy resin or polyimide, used to form the plurality of second acoustic matching layers 2b, is prepared. The plurality of electrical terminals 7 having an overall ribbon-like shape is prepared, in which a conductive film 7b made of copper or the like is deposited on one main surface of an insulating film 7a made of a high-polymer material such as polyimide. The electrical terminal 9 for grounding is prepared, in which a conductive film (thickness is preferably 5 micrometers or less to minimize effect on characteristics) 9b made of copper or the like is deposited on one main surface of an insulating film 9a, made of a high-polymer material such as polyimide. The high-polymer material, such as epoxy resin and polyimide, used to form the second acoustic matching layers 2b is an insulating member. However, a conductive member can be used instead. Any material that is electrically conductive can be used for the conductive films 7b and 9b. The material is not limited to metal.

As shown in FIG. 4A, the plurality of electrical terminals 7 for signals are placed on the front surface of the backing material 3 at a predetermined interval in the X direction. The piezoelectric plate material for forming the piezoelectric elements 1 is laminated on the plurality of electrical terminals 7 for signals. The plate material for forming the first acoustic matching layers 2a, the electrical terminal 9 for grounding, and the plate material for forming the second acoustic matching layers 2b are successively laminated on the front surface of the piezoelectric plate material. The laminate is integrally fixed. In this case, the one main surface of the insulating film 7a of the plurality of electrical terminals 7 for signals mounted between the backing material 3 and the piezoelectric plate material faces the piezoelectric plate material side (upper side in FIG. 4A), such that the conductive film 7b deposited on the one main surface of each insulating film 7a is in contact with the signal electrode 6 formed on the piezoelectric plate material and the insulating film 7a is in contact with the backing material 3. The one main surface of the insulating film 9a of the electrical terminal 9 for grounding mounted between the plate material for forming the first acoustic matching layers 2a and the plate material for forming the second acoustic matching layers 2b faces the first acoustic matching layer 2a side, such that the conductive film 9b formed on the one main surface of the insulating film 9a is in contact with the first acoustic matching layer 2a.

In this way, after the backing material 3, the plurality of electrical terminals 7 for signals, the piezoelectric plate material for forming the piezoelectric elements 1, the plate material for forming the first acoustic matching layers 2a, the electrical terminal 9 for grounding, and the plate material for forming the second acoustic matching layers 2b are integrally fixed, a slicing machine or the like is used to form a plurality of grooves having a depth from the front surface of the second acoustic matching layer 2b to the front surface section of the backing material 3. In other words, division grooves are formed that divide the laminate into a plurality of piezoelectric element units, a single unit including the second acoustic matching layer 2b, the electrical terminal 9 for grounding, the first acoustic matching layer 2a, the piezoelectric plate material, the electrical terminal 7 for signals, and a portion of the backing 3. In this case, the division grooves are formed in intermediate sections between the electrical terminals 7 for signals disposed at a predetermined interval in the X direction. As a result, a piezoelectric element row in which the piezoelectric element units are arrayed in parallel is formed. Next, each division groove is filled with a material (not shown), such as silicone rubber or urethane rubber, that has low acoustic coupling. Furthermore, the third acoustic matching layer 2c is mounted on the uppers surface of the second acoustic matching layers 2b and the sections in which the division grooves are filled.

The third acoustic matching layer 2c is mounted in a connected state without being divided, as shown. As a material for the third acoustic matching layer 2c, a material is used in which the main constituent is a rubber elastic member, such as silicone rubber, chloroprene rubber, ethylene propylene copolymer rubber, acrylonitrile butadiene copolymer rubber, and urethane rubber. Moreover, the acoustic lens 4, using a material such as silicone rubber, is mounted on the upper surface of the third acoustic matching layer 2c, as required. In an ultrasound probe that does not include the backing material 3, the member replacing the backing material 3 is removed at this stage.

The third acoustic matching layer 2c can be divided with the piezoelectric elements 1, in the same manner as the first acoustic matching layers 2a and the second acoustic matching layers 2b. The second acoustic matching layers 2b and the third acoustic matching layer 2c can be either an insulating member or a conductive member.

Here, a configuration is described in which the electrical terminal 9 for grounding and the ground electrode 5 formed on the piezoelectric element 1 are electrically connected as a result of the electrical terminal 9 for grounding, in which the conductive film 9b is deposited on the insulating film 9a, being inserted between the first acoustic matching layer 2a and the second acoustic matching layer 2b, and the conductive film 9b of the electrical terminal 9 for grounding and the conductive member of the first acoustic matching layer 2a coming into contact. However, similar operations can also be performed by a conductive member being used as the second acoustic matching layer 2b, the electrical terminal 9 for grounding on which the conductive film 9b is deposited being mounted on the front surface of the second acoustic matching layer 2b, and the electrical terminal 9 for grounding and the ground electrode 5 formed on the piezoelectric element 1 being electrically connected, via the first acoustic matching layer 2a and the second acoustic matching layer 2b.

Operations of the ultrasound probe 10C configured as described above will be described below.

The signal electrode 6 formed on the back surface of the piezoelectric element 1 is electrically connected to one end of a cable (not shown), via the electrical terminal 7 for signals. The ground electrode 5 formed on the front surface of the piezoelectric element 1 is also electrically connected to one end of a cable (not shown), via the conductive member in the composite material of the first acoustic matching layer 2a and the electrical terminal 9 for grounding. The other end of each cable is connected to a main body section of an ultrasonic diagnostic apparatus (not shown). As a result, regular pulse voltage generated by the main body section of the ultrasonic diagnostic apparatus is applied to the piezoelectric element 1, and an ultrasonic wave is emitted. In addition, a received echo of an ultrasonic wave is converted to an electrical signal and transmitted to the main body section of the ultrasonic diagnostic apparatus.

In this case, the conductive member of the first acoustic matching layer 2a, details of which will be described hereafter, is merely required to have a shape that electrically connects the ground electrode 5 formed on the piezoelectric element 1 and the conductive film 9b of the electrical terminal 9 for grounding. The conductive member is not limited to a particular shape. A configuration is preferred in which the conductive member of the first acoustic matching layer 2a allows the ground electrode 5 of the piezoelectric element 1 and the conductive film 9b of the electrical terminal 9 for grounding to be electrically connected at two or more areas of a single piezoelectric element 1. When the number of conductive members 20 is large, malfunction caused by disconnection of a signal transmission line becomes infrequent, even when both the ground electrode 5 and the piezoelectric element 1 are broken. High reliability is achieved.

Moreover, a main purpose of the insulating member or semiconductive member 21 of the first acoustic matching layer 2a is to bring the acoustic impedances closer to a matching state. Therefore, when the three-layer acoustic matching layer is provided as according to the fourth embodiment, a range of a value used for each acoustic impedance of the first acoustic matching layer 2a, the second acoustic matching layer 2b, and the third acoustic matching layer 2c is selected based on respective target frequency characteristics. For example, in Japanese Patent Application Publication No. S60-53399, a range of 12.6 to 18.1 MRayl, a range of 3.8 to 6.0 MRayl, and a range of 1.7 to 2.4 MRayl are respectively indicated as the acoustic impedance of the first acoustic matching layer 2a, the second acoustic matching layer 2b, and the third acoustic matching layer 2c. In Japanese Patent Application Publication No. S60-185499, a range of 5 to 15 MRayl, a range of 1.9 to 4.4 MRayl, and a range of 1.6 to 2 MRayl are respectively indicated as the acoustic impedance of the first acoustic matching layer 2a, the second acoustic matching layer 2b, and the third acoustic matching layer 2c. Moreover, in Japanese Patent Application Publication No. 2003-125494, 19.7 MRayl, 7.4 MRayl, and 2.44 MRayl are respectively indicated as the acoustic impedance of the first acoustic matching layer 2a, the second acoustic matching layer 2b, and the third acoustic matching layer 2c. Therefore, a material having an acoustic impedance value within a range of about 5 to 20 MRayl is used as the first acoustic matching layer 2a in the three-layer type acoustic matching layer. As the number of layers in the acoustic matching layer increases, a broader band in the frequency characteristics and a higher sensitivity can be achieved. At the least, a broader frequency band can be achieved with the three-layer acoustic matching layer type, compared to the two-layer acoustic matching layer type.

As an example of each coupled structures formed by the conductive member 20 and the insulating member or semiconductive member 21 of the first acoustic matching layer 2a configured by the composite material including the conductive member and the insulating member or semiconductive member, the 1-3 type, or the 2-2 type, shown in FIG. 3C and FIG. 3D and described according to the third embodiment, or the above-described 3-1 type structure can be used.

As the conductive member 20 of the first acoustic matching layer 2a, a metal, such as copper, aluminum, silver, gold, and nickel, a high-polymer material in which, for example, metal such as gold, silver, copper, and aluminum, or carbon power is combined with a high-polymer compound such as epoxy resin and given conductivity, graphite, carbon, and the like are used. As the insulating member or semiconductive member 21 of the first acoustic matching layer 2a, ceramics such as glass, crystallized glass, epoxy resin including a high concentration of tungsten powder, lead niobate ceramics, workable ceramics (free-cutting ceramics), monocrystal or polycrystal silicon, quartz crystal, and barium titanate, and the like are used.

The conductive member 20 and the insulating member or semiconductive member 21 can be materials other than those described above, as long as the material can achieve the objects of the present invention. The acoustic impedances of the composite materials having the 1-3 type coupled structure, the 2-2 type coupled structure, and the 3-1 type coupled structure, including the conductive member 20 and the insulating member or semiconductive member 21, are determined by respective volume amounts, as described according to the second embodiment. For example, in a manner similar to the graph in FIG. 2C according to the second embodiment, a desired value within a range of 15.3 and 38 MRayl can be obtained as the acoustic impedance of the composite material by the volume amount being arbitrarily selected when silver having an acoustic impedance value of 38 MRayl is used as the conductive member 20 and an X-cut quartz crystal having an acoustic impedance value of 15.3 MRayl is used as the insulating member 21. Regarding the acoustic impedance within this range, a volume amount is present that has a range equivalent to 5 to 20 MRayl that is a range of the value required for the first acoustic matching layer 2a of the three-layer acoustic matching layer. A material created within this range provides a function as the first acoustic matching layer 2a. As another function provided by the first acoustic matching layer 2a according to the fourth embodiment, a configuration is achieved in which the conductive members 20 in the first acoustic matching layer 2a can electrically connect the ground electrode 5 of the piezoelectric element 1 and the conductive member of the electrical terminal 9 for grounding. Therefore, a configuration in which the electrical terminal can be taken out is used.

When the coupled structure is the 1-3 type structure, the 2-2 type structure, and the 3-1 type structure, the acoustic impedance value is within the range of the respective acoustic impedances of the two types of materials. A material having a desired acoustic impedance can be obtained by the volume amount of each material being changed. According to the fourth embodiment, a first acoustic matching layer 2a having a coupled structure formed by the conductive member 20 and the insulating member or semiconductive member 21 is described. However, similar effects can clearly be achieved when two or more types of conductive member 20 materials and insulating member or semiconductive member 21 materials are used. The coupled structure is not limited to that including one type of each or, in other words, a total of two types of materials.

To allow the composite material including the conductive member 20 and the insulating member or semiconductive member 21 having the 1-3 type, the 2-2 type, or 3-1 type coupled structure to function as the first acoustic matching layer 2a, the width and placement interval of the conductive members 20 are set such that the composite material can integrally carry the ultrasonic waves. When the volume amount of the conductive member 20 is small, the width and placement interval of the conductive members 20 are not required to be taken into consideration. The material used for the conductive member 20 can be selected based mainly on its electrical connection function.

As shown in FIG. 4A, a configuration is used in which the third acoustic matching layer 2c is not divided in correspondence with the piezoelectric elements 1. However, similar effects can naturally be achieved in a configuration in which the third acoustic matching layer 2c is divided. Therefore, the configuration is not limited to that shown in FIG. 4A.

As described above, as a result of the composite material, in which the conductive member and the insulating member or the semiconductive member are combined, being used as the acoustic matching layer provided on the subject side of the piezoelectric elements, the acoustic impedance of the acoustic matching layer can be set to a desired value, and the frequency band can be broadened. As a result, a high-resolution diagnostic image can be obtained. Moreover, because the electrical terminal can be taken out from the conductive member included in the composite material, an ultrasound probe can be achieved that is highly reliable and has excellent operability.

According to the fourth embodiment, although a columnar shape is used for the conductive members 20 in the 1-3 type coupled structure, similar effects can be achieved even when other shapes, such as a rectangular column or a sphere, are used. Similar effects can also be achieved in a configuration in which a conical shape, such as a cone formed in the Z direction, is used for the conductive members 20 in the 1-3 type coupled structure, and the acoustic impedance continuously changes in relation to the thickness in the Z direction.

According to the fourth embodiment, when the conductive members 20 and the insulating members or semiconductive members 21 in the 2-2 type coupled structure are formed with uniform widths in the Z direction is described. However, similar effects can be achieved in a configuration in which the members continuously change in width in the Z direction, forming a so-called wedge shape, and the acoustic impedance continuously changes in relation to the thickness in the Z direction.

According to the fourth embodiment, when the conductive members 20 and the insulating members or semiconductive members 21 in the 1-3 type coupled structure, the 2-2 type coupled structure, and the 3-1 type coupled structure are arrayed in an alternating manner at almost even intervals is described. However, similar effects can be achieved at random intervals or in a random array. Moreover, according to the fourth embodiment, a configuration is described in which, to exchange electrical signals with the ground electrode 5 of the piezoelectric element 1, the electrical terminal 9 for grounding is provided on the front surface of the first acoustic matching layer 2a, with the first acoustic matching layer 2a between the electrical terminal 9 for grounding and the ground electrode 5. However, instead, similar effects can be achieved by a configuration in which the conductive member is formed on both surfaces or on one surface of the first acoustic matching layer 2a in the Z direction by sputtering, plating, printing, or the like, and the electrical terminal 9 for grounding is connected to this area.

According to the fourth embodiment, a configuration in which the plurality of piezoelectric elements 1 are arrayed in a one-dimensional manner is described. However, similar effects can also be achieved in a configuration that is a so-called two-dimensional array, in which the plurality of piezoelectric elements 1 are arrayed in a two-dimensional manner. Moreover, according to the fourth embodiment, when two types of conductive members and the insulating members or semiconductive members are used is described. However, similar effects can also be achieved when two or more types of materials are used, such as two types of conductive members and one to three types of insulating members.

According to the fourth embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Fifth Embodiment>

Figure 5A:
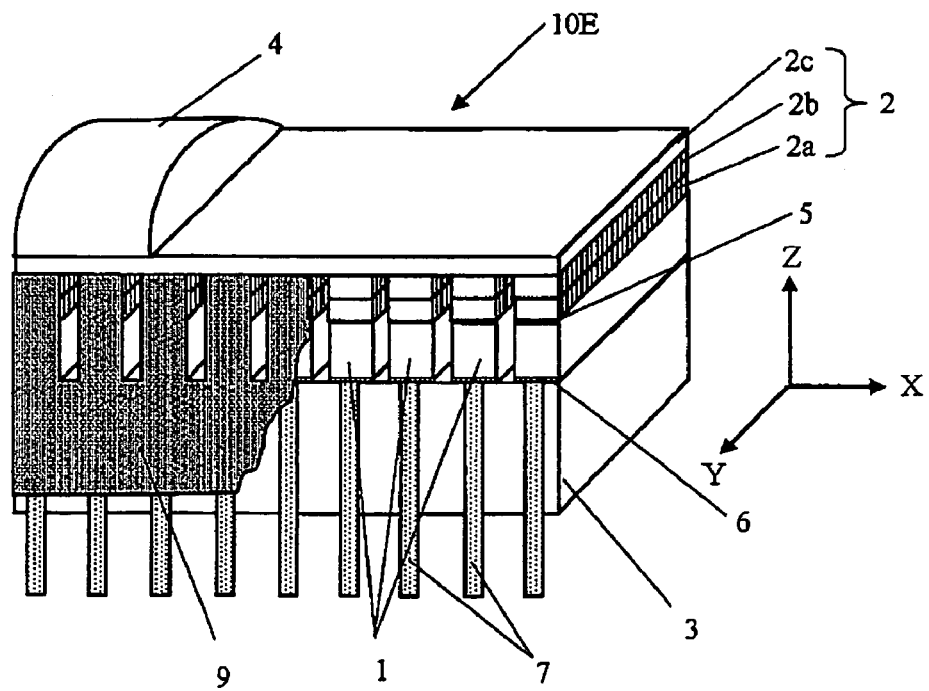
FIG. 5A is a perspective view of a configuration of an ultrasound probe according to a fifth embodiment of the present invention in which a portion thereof is a cutaway view.
Figure 5B:
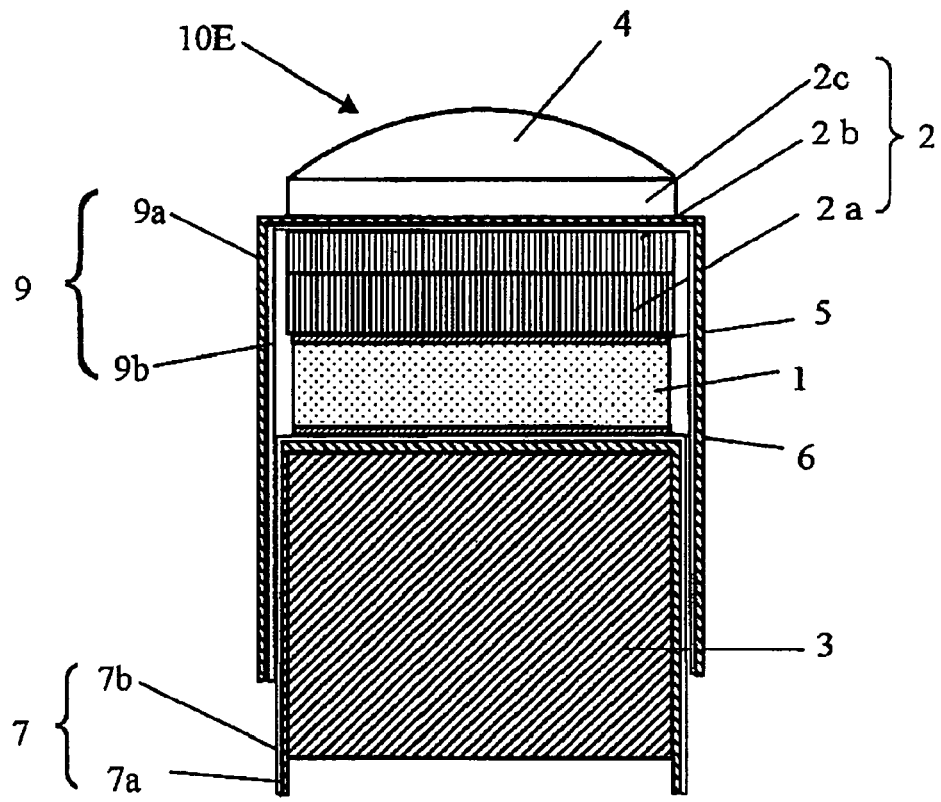
FIG. 5B is a cross-sectional view of an ultrasound probe shown in FIG. 5A.

Next, a fifth embodiment of the present invention will be described. FIG. 5A is a perspective view of a configuration of an ultrasound probe according to the fifth embodiment of the present invention in which a portion thereof is a cutaway view. FIG. 5B is a cross-sectional view of the ultrasound probe shown in FIG. 5A in which a cross-section taken along a Y-Z plane, among three directions, X, Y, and Z, shown in FIG. 5A, is viewed from the X direction.

An ultrasound probe 10E shown in FIG. 5A and FIG. 5B include the plurality of piezoelectric elements 1 arrayed in the X direction, among X, Y, and Z shown in FIG. 5A, the acoustic matching layer 2 including a plurality of first acoustic matching layers 2a laminated on the front surface in the Z direction that is the subject side in correspondence with each piezoelectric element 1, a plurality of second acoustic matching layers 2b, and a third acoustic matching layer 3c laminated on the second acoustic matching layers 2b in a shared manner, the backing material 3 provided on the back surface of the piezoelectric elements 1 as required, the acoustic lens 4 provided on the front surface of the acoustic matching layer 2 (2a, 2b, and 2c), also as required, the plurality of electrical terminals 7 for signals inserted between the piezoelectric elements 1 and the backing material 3, and the electrical terminal 9 for grounding inserted between the second acoustic matching layer 2b and the third acoustic matching layer 2c. Respective functions of these constituent elements are similar to the functions of the elements configuring a conventional ultrasound probe.

Compared with the fourth embodiment, according to the fifth embodiment, lamination structures of the piezoelectric elements 1, the first acoustic matching layers 2a, and the third acoustic matching layer 2c are the same. Basic differences are that a conductive member or, in a manner similar to the first acoustic matching layers 2a, a composite material including the conductive member and the insulating member or the semiconductive member is used in the second acoustic matching layers 2b, and the electrical terminal 9 for grounding is provided on the upper surface of the second acoustic matching layers 2b. In the electrical terminal 9 for grounding, the metal film 9b made of copper or the like is deposited on the one main surface of the insulating film 9a configured by a high-polymer material such as polyimide. As a result of a configuration such as this, the electrical terminal 9 for grounding and the ground electrode 5 formed on the piezoelectric elements 1 can be electrically connected, via the first acoustic matching layers 2a and the second acoustic matching layers 2b.

When the composite material is used for both the first acoustic matching layers 2a and the second acoustic matching layers 2b, a configuration is required in which at least each conductive member section of the acoustic matching layers 2a and 2b are electrically connected. The coupled structures of the composite materials of the first acoustic matching layers 2a and the second acoustic matching layers 2b are not necessarily required to be the same structure. For example, the coupled structure of the first acoustic matching layers 2a can be the 1-3 type and the coupled structure of the second acoustic matching layers 2b can be the 2-2 type. All that is required is that the conductive member sections of both acoustic matching layers are electrically connected, the electrical terminal 9 for grounding and the ground electrode 5 formed on the piezoelectric elements 1 are electrically connected, and each has an acoustic impedance value as an acoustic matching layer.

As the second acoustic matching layers 2b, a conductive member, such as graphite can be used. Alternatively, the composite material including a conductive member and an insulating member or semiconductive member can be used. When the composite material including the conductive member and the insulating member or semiconductive member is used, for example, silver having an acoustic impedance of 38 MRayl can be used as the conductive member 20, epoxy resin having an acoustic impedance of 3 MRayl can be used as the insulating member 21. The acoustic impedance can be arbitrarily set by the volume amounts being changed. For example, an acoustic impedance of a value near 6 MRayl can be obtained. This is also possible with composite materials having any of the 1-3 type, the 2-2 type, and the 3-1 type coupled structures.

On the other hand, according to the fifth embodiment, when a material having an acoustic impedance of about 3 MRayl, such as polyimide, is used as the insulating film that is a base material of the electrical terminal 9 for grounding mounted on the front surface of the second acoustic matching layers 2b, the acoustic impedance of the material is a value between that of the second acoustic matching layer 2b and that of the third acoustic matching layer 2c or a value near this value. Therefore, acoustic mismatch is eliminated, and good frequency characteristics are more easily obtained.

As described above, in the configuration of the three-layer acoustic matching layer provided on the subject side surface of the piezoelectric elements, as a result of the composite material including the conductive member and the insulating member or semiconductive member being used as the first and second acoustic matching layers, the acoustic impedances of both the first and second acoustic matching layers can be set to desired values. As a result, the frequency band can be broadened, thereby allowing a high-resolution, diagnostic image to be obtained. The electrical terminal 9 for grounding can be electrically connected to the ground electrode 5 via each conductive member in the first and second acoustic matching layers. Therefore, an ultrasound probe can be achieved that is highly reliable and has excellent operability.

According to the fifth embodiment, the first acoustic matching layers 2a and the second acoustic matching layers 2b having coupled structures including the conductive member 20 and the insulating member or semiconductive member 21 that are respectively one type of material is described. However, similar effects can also clearly be achieved when two or more types of the conductive member 20 and the insulating member or semiconductive member 21 are used. The coupled structure is not limited to that including one type of material each as the conductive member 20 and the insulating member or semiconductive member 21.

According to the fifth embodiment, although a columnar shape is used for the conductive members in the 1-3 type coupled structure, similar effects can be achieved even when other shapes, such as a rectangular column or a sphere, are used. According to the fifth embodiment, although a columnar shape is used in the conductive members 20 in the 1-3 type coupled structure, similar effects can also be achieved in a configuration in which a conical shape, such as a cone formed in the Z direction, is used and the acoustic impedance continuously changes in relation to the thickness in the Z direction.

According to the fifth embodiment, when the conductive members 20 and the insulating members or semiconductive members 21 in the 1-3 type coupled structure, the 2-2 type coupled structure, and the 3-1 type coupled structure are arrayed in an alternating manner at almost even intervals is described. However, similar effects can be achieved at random intervals or in a random array.

According to the fifth embodiment, a configuration is described in which, to exchange electrical signals with the ground electrode 5 of the piezoelectric element 1, electrical terminals are provided on the front surfaces of the first acoustic matching layer 2a and the second acoustic matching layer 2b, via each conductive member 20 of the first acoustic matching layer 2a and the second acoustic matching layer 2b. However, instead, similar effects can be achieved by a configuration in which the conductive member is formed on both surfaces or on one surface of the second acoustic matching layer 2b in the Z direction by sputtering, plating, printing, or the like, and the electrical terminal is connected to this area.

According to the fifth embodiment, a configuration in which the plurality of piezoelectric elements 1 are arrayed in a one-dimensional manner is described. However, similar effects can also be achieved in a configuration that is a so-called two-dimensional array, in which the plurality of piezoelectric elements 1 are arrayed in a two-dimensional manner.

According to the fifth embodiment, an ultrasound probe is described that includes an acoustic matching layer 2 having a total of three layers in which the second acoustic layer 2b and the third acoustic matching layer 2c are laminated on the front surface of the first acoustic matching layer 2a. However, similar effects as those described above can be achieved by a configuration in which the acoustic matching layer 2 includes first to n-th acoustic matching layers, in which n is an integer of three or more, and an electrical terminal is mounted between the second acoustic matching layer and the third acoustic matching layer.

According to the fifth embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Sixth Embodiment>

Figure 6A:
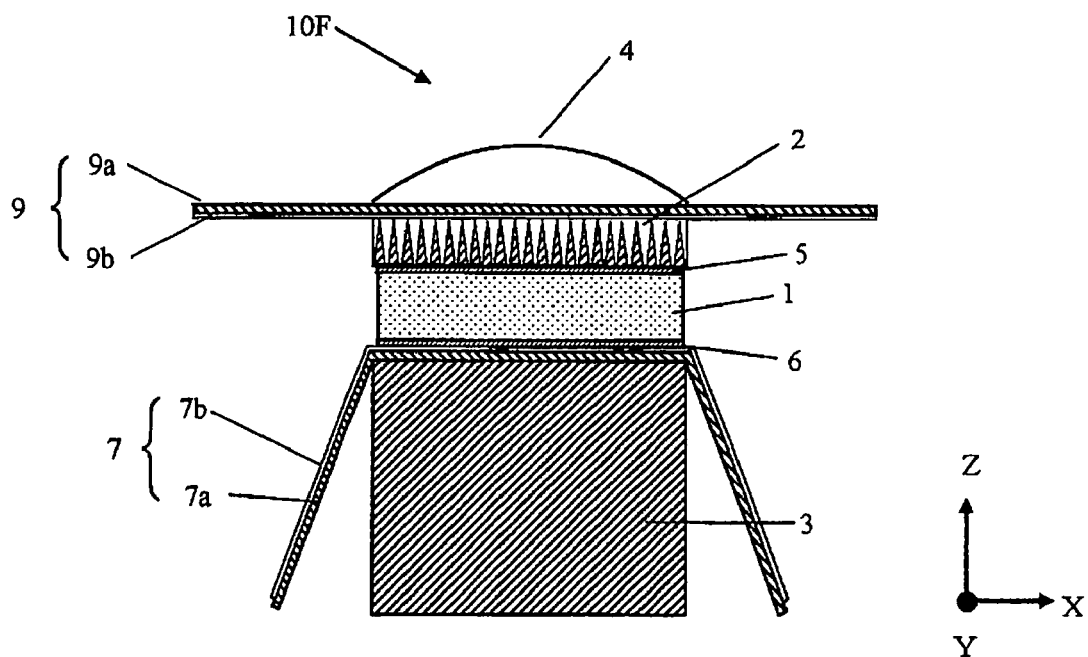
FIG. 6A is a cross-sectional view of a configuration of an ultrasound probe according to a sixth embodiment of the present invention in which a portion thereof is a cutaway view.
Figure 6B:
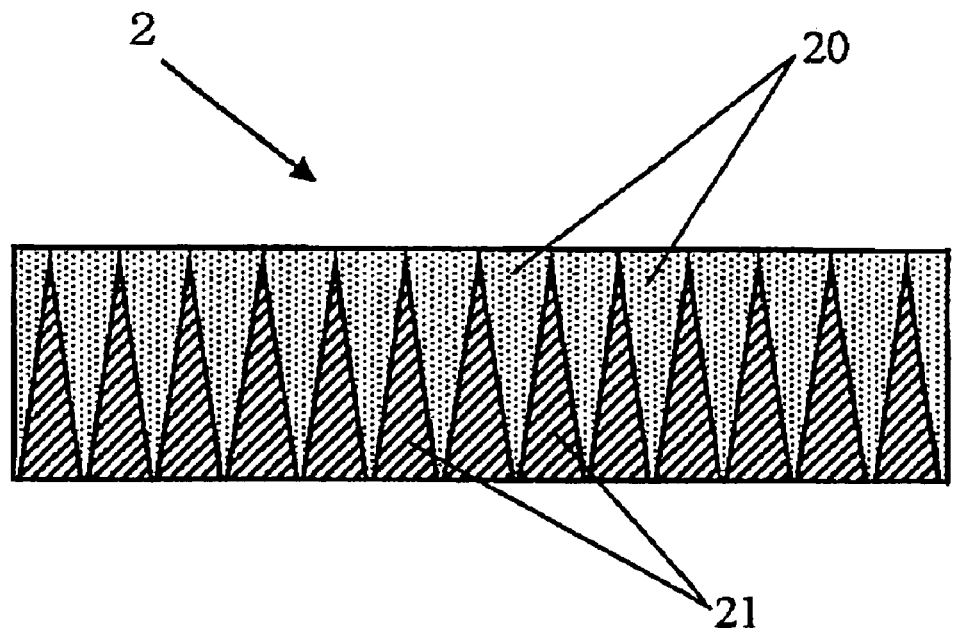
FIG. 6B is a cross-sectional view of a configuration example of an acoustic matching layer configuring an ultrasound probe shown in FIG. 6A.

FIG. 6A is a cross-sectional view of a configuration of an ultrasound probe according to a sixth embodiment of the present invention. FIG. 6B is a cross-sectional view of a configuration example of an acoustic matching layer configuring the ultrasound probe shown in FIG. 6A.

In FIG. 6A, an ultrasound probe 10F includes the plate-shaped piezoelectric element 1, the acoustic matching layer 2 laminated on the front surface (upper side in FIG. 6A) of the piezoelectric element 1, the backing material 3 mounted on the back surface (lower side in FIG. 6A) of the piezoelectric element 1 as required, and the acoustic lens 4 mounted on the front surface of the acoustic matching layer 2, also as required. Respective functions of these constituent elements are similar to the functions of the elements configuring a conventional ultrasound probe.

Among the constituent elements of the ultrasound probe 10F, the piezoelectric element 1 is made of a piezoelectric ceramic, such as a PZT system, a piezoelectric monocrystal, such as a PZN-PT system or a PMN-PT system, or a composite piezoelectric material that is a combination of the piezoelectric ceramic, the piezoelectric monocrystal, and a high-polymer material. Alternatively, the piezoelectric element 1 is made of a piezoelectric material of a high-polymer material represented by PVDF and the like. The ground electrode 5 is formed on the front surface of the piezoelectric element 1. The signal electrode 6 is formed on the back surface of the piezoelectric element 1. The ground electrode 5 and the signal electrode 6 are each formed by deposition of gold or silver, sputtering, or silver baking.

The electrical terminal 7 for signals is inserted between the signal electrode 6, formed on the piezoelectric element 1, and the backing material 3. In the electrical terminal 7 for signals, the metal film 7b made of copper or the like is deposited on one main surface of the insulating film 7a made of a high-polymer material such as polyimide. In this case, the one main surface of the insulating film 7a faces the piezoelectric element 1 side, such that the metal film 7b of the electrical terminal 7 for signals is in contact with the signal electrode 6 formed on the piezoelectric element 1, and the insulating film 7a of the electrical terminal 7 for signals is in contact with the backing material 3. On the other hand, on the front surface of the ground electrode 5 formed on the piezoelectric element 1, the acoustic matching layer 2 made of the composite material including the conductive member 20 and the insulating member or semiconductive member 21, and the electrical terminal 9 for grounding are successively laminated. In the electrical terminal 9 for grounding, the conductive film (thickness is preferably 5 micrometers or less to minimize effect on characteristics) 9b made of copper or the like is deposited on one main surface of the insulating film 9a made of a high-polymer material such as polyimide. In this case, the one main surface of the insulating film 9a faces the acoustic matching layer 2 side, such that the conductive film 9b of the electrical terminal 9 for grounding is in contact with the conductive member 20 in the composite material configuring the acoustic matching layer 2. The acoustic lens 4, for which a material such as silicone rubber is used, is mounted on the front surface of the acoustic matching layer 2, as required.

Operations of the ultrasound probe 10F configured as described above will be described.

The signal electrode 6 formed on the piezoelectric element 1 is electrically connected to one end of a cable (not shown), via the electrical terminal 7 for signals. The ground electrode 5 on the piezoelectric element 1 is also electrically connected to one end of a cable (not shown), via the conductive member 20 in the composite material of the acoustic matching layer 2 and the electrical terminal 9 for grounding. The other end of each cable is connected to a main body section of an ultrasonic diagnostic apparatus (not shown). As a result, regular pulse voltage generated by the main body section of the ultrasonic diagnostic apparatus is applied to the piezoelectric element 1, and an ultrasonic wave is emitted. In addition, a received echo of an ultrasonic wave is converted to an electrical signal and transmitted to the main body section of the ultrasonic diagnostic apparatus.

In FIG. 6B, as the acoustic matching layer 2 configured by the composite material including the conductive members 20 and the insulating members or semiconductive members 21, a material of which the acoustic impedance is between the acoustic impedance of the piezoelectric element 1 and the acoustic impedance of the subject (such as a living body) is selected. A configuration is used in which the shape (volume) of the insulating members or semiconductive members 21 continuously changes in relation to the thickness direction (vertical direction in FIG. 6B). In FIG. 6B, a shape is used in which the volume is large at the lower side and decreases towards the upper side (such as a conical shape, a triangular pyramid, and a rectangular pyramid). The conductive member 20 fills the gaps between the insulating members or semiconductive members 21. For example, when a material having a larger acoustic impedance value than the acoustic impedance of the conductive member 20 is used as the insulating member or semiconductive member 21, in FIG. 6B, the acoustic impedance value is largest at the lower side because the volume is large. The volume of the insulating member or semiconductive member 21 gradually decreases towards the upper side, and the volume of the conductive member 20 increases. As a result, the acoustic impedance gradually decreases. In other words, a configuration is used in which the acoustic impedance of the acoustic matching layer 2 continuously changes in the vertical direction. When, in the configuration in FIG. 6A, the acoustic impedance is large at the lower side in FIG. 6A and gradually decreases towards the upper side, a configuration is naturally that in which the piezoelectric element 1 side is on the lower side and the subject side is on the upper side.

Because a configuration is used in which the shape of the acoustic matching layer 2 continuously changes in the thickness direction in this way, the acoustic matching layer 2 has a characteristic in which the acoustic impedance continuously changes in relation to the thickness direction (a direction from the piezoelectric element 1 to the subject). At a section of the acoustic matching layer 2 positioned on the ground electrode 2 side of the piezoelectric element 1, the acoustic impedance is a large value close to the acoustic impedance of the piezoelectric element 1. The acoustic impedance of the acoustic matching layer 2 at a section positioned on the subject side (the upper side in FIG. 6A) is a value close to the acoustic impedance of the subject. As a result of the acoustic matching layer 2 being used in which the acoustic impedance is a continuous gradient in this way, the frequency band can be broadened. Moreover, because the thickness of the acoustic matching layer 2 is not dependent on the frequency, the acoustic matching layer 2 can achieve effects as an acoustic matching layer if the thickness is about half of the wavelength of a center frequency or more. Frequency characteristics have little correlation with the thickness.

A configuration is used in which the conductive members 20 of the acoustic matching layer 2 are electrically connected to one electrode of the piezoelectric element 1. The conductive film 9b of the electrical terminal 9 for grounding is in contact with the outer surface of the conductive members 20, and the conductive film 9b and the conductive members 20 are electrically connected. Signals are received and taken out from the electrical terminal 9 for grounding. As a coupled structure of the insulating members or semiconductive members 21 and the conductive members 20 of the acoustic matching layer 2, the 2-2 type, the 1-3 type, and the 3-1 type coupled structures described according to the second embodiment are preferable. For example, a characteristic can be achieved in which, when a silicon monocrystal having an acoustic impedance of about 19.7 MRayl is used as a semiconductor serving as the insulating member or semiconductive member 21, and a conductive adhesive, Echobond 56C (Emerson and Cummings, Inc.), having an acoustic impedance of about 6.5 MRayl is used as the conductive member 20, the acoustic impedance is 19.7 MRayl in a section in which the volume amount of the silicon monocrystal is almost 100%. As the volume amount of the silicon monocrystal gradually decreases and the volume amount of the conductive adhesive gradually increases, the acoustic impedance becomes closer to 6.5 MRayl.

Here, as the insulating member or semiconductive member 21 of the acoustic matching layer 2, ceramics such as glass, crystallized glass, epoxy resin including a high concentration of tungsten powder, lead niobate ceramics, workable ceramics (free-cutting ceramics), monocrystal or polycrystal silicon, quartz crystal, and barium titanate, and the like are used. As the conductive member 20 of the acoustic matching layer 2, a metallic material, such as graphite, graphite filled with metal such as copper, aluminum, silver, gold, and nickel, a high-polymer material in which, for example, metal such as gold, silver, copper, and aluminum, or carbon power is combined with a high-polymer compound such as epoxy resin and given conductivity, graphite, carbon, and the like are used.

The conductive member 20 and the insulating member or semiconductive member 21 are not limited to the above-described materials. Other materials can be used as long as the materials have similar acoustic impedance as the above-described materials.

As a result of the composite material including the conductive member and the insulating member or semiconductive member being provided as the acoustic matching layer provided on the subject side of the piezoelectric element, the desired acoustic impedance of the acoustic matching layer can be a continuous gradient. As a result, the frequency band can be broadened, thereby allowing a high-resolution, diagnostic image to be obtained. The electrical terminal can be connected at a plurality of areas of the piezoelectric element through the conductive members in the acoustic matching layer that is the composite material. Therefore, an ultrasound probe can be achieved that is highly reliable and has excellent operability.

According to the sixth embodiment, when the conductive members 20 and the insulating members or semiconductive members 21 are arrayed in an alternating manner at almost even intervals, as shown in FIG. 6B, is described. However, similar effects can be achieved at random intervals or in a random array.

According to the sixth embodiment, a configuration is described in which, to exchange electrical signals with the ground electrode 5 of the piezoelectric element 1, the electrical terminal 9 for grounding is provided on the front surface of the acoustic matching layer 2, with the acoustic matching layer 2 between the electrical terminal 9 for grounding and the ground electrode 5. However, instead, similar effects can be achieved by a configuration in which the conductive member is formed on both surfaces or on one surface of the acoustic matching layer 2 in the Z direction by sputtering, plating, printing, or the like, and the electrical terminal 9 for grounding is connected to this area.

According to the sixth embodiment, as the acoustic matching layer 2, a coupled structure is used including the conductive member 20 and the insulating member or semiconductive member 21 each made of one type of material. However, similar effects can clearly be achieved even when at least one of the conductive member 20 and the insulating member or semiconductive member 21 is made of two types of materials or more. The structure is not limited to a coupled structure including one type of material for each member.

According to the sixth embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

<Seventh Embodiment>

Figure 7A:
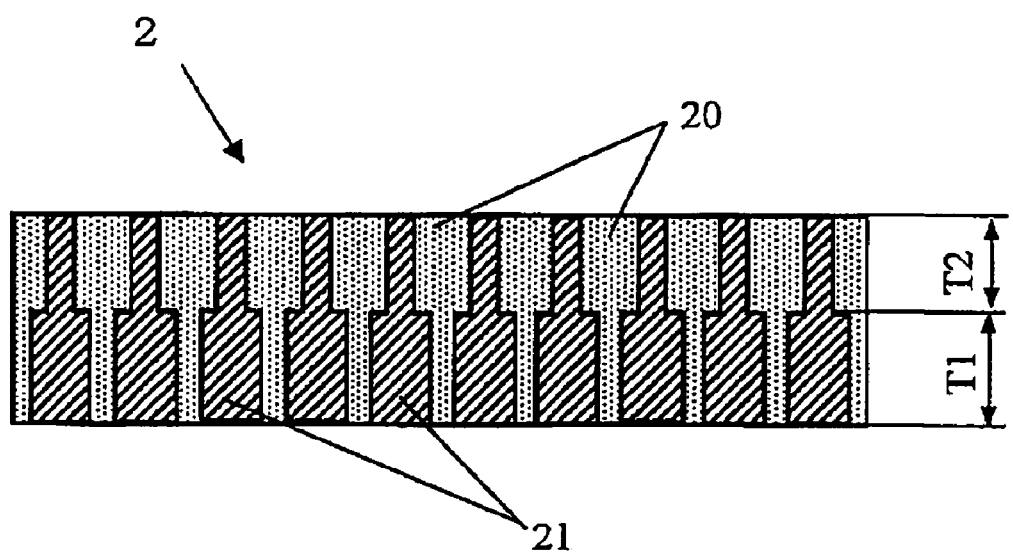
FIG. 7A is a cross-sectional view of a configuration example of an acoustic matching layer configuring an ultrasound probe according to a seventh embodiment of the present invention.

FIG. 7A is a cross-sectional view of a configuration of an acoustic matching layer configuring an ultrasound probe according to a seventh embodiment of the present invention. A rough cross-sectional view of the ultrasound probe is the same as that in FIG. 6A described according to the sixth embodiment, aside from a difference in the configuration of the acoustic matching layer 2. Therefore, the ultrasound probe will be described with reference to FIG. 6A. The acoustic matching layer section will be described with reference to FIG. 7A.

In FIG. 6A, the ultrasound probe 10F includes the plate-shaped piezoelectric element 1, the acoustic matching layer 2 laminated on the front surface (upper side in FIG. 6A) of the piezoelectric element 1, the back surface load material 3 mounted on the back surface (lower side in FIG. 6A) of the piezoelectric element 1 as required, and the acoustic lens 4 mounted on the front surface of the acoustic matching layer 2, also as required. Respective functions of these constituent elements are similar to the functions of the elements configuring a conventional ultrasound probe. Constituent elements and operations of the ultrasound probe 10F are described according to the sixth embodiment. Therefore, descriptions thereof are omitted.

In FIG. 7A, as the acoustic matching layer 2 configured by the composite material including the conductive member 20 and the insulating member or semiconductive member 21, a material having an acoustic impedance between the acoustic impedance of the piezoelectric element 1 and the acoustic impedance of the subject (such as a living body) is selected. A configuration is used in which the shape (volume amount) of the insulating member or semiconductive member 21 variably changes in stages in relation to the thickness direction (the vertical direction in FIG. 7A), such as the width being two stages in FIG. 7A. A shape is used in which a bottom stage (T1 area) has a wide width, and the width decreases at a top stage (T2 area). The conductive member 20 fills the gaps between the insulating members or semiconductive members 21. For example, when the insulating member or semiconductive member 21 is a material having a larger acoustic impedance value than the acoustic impedance of the conductive member 20, the acoustic impedance value becomes large because the width in the T1 area is wide. The width in the T2 area becomes narrow. On the other hand, the width of the conductive member 20 becomes the opposite. The acoustic impedance becomes closer to the respective acoustic impedance of the member having the wider width (volume). The acoustic impedance can be changed in stages by the volume amounts of the conductive member 20 and the insulating member or semiconductive member 21 in the T1 and T2 areas. Therefore, in a two-stage configuration shown in FIG. 7A, a two-layer acoustic matching layer is configured. Respective thicknesses of T1 and T2 are naturally set based on a thickness of one-fourths wavelength.

As shown in FIG. 6A, a configuration is used in which the conductive members 20 of the acoustic matching layer 2 are electrically connected to one electrode of the piezoelectric element 1. The conductive film 9b of the electrical terminal 9 for grounding is in contact with the outer surface of the conductive members 20, and the conductive film 9b and the conductive members 20 are electrically connected. Signals are received and taken out from the electrical terminal 9 for grounding. As a coupled structure of the conductive members 20 and the insulating members or semiconductive members 21 in the acoustic matching layer 2 shown in FIG. 7A, the 2-2 type, the 1-3 type, and the 3-1 type coupled structures described according to the second embodiment are preferable.

As a result of the composite material including the conductive member and the insulating member or semiconductive member being provided as the acoustic matching layer provided on the subject side of the piezoelectric element, as described above, the desired acoustic impedance of the acoustic matching layer can be changed in stages. As a result, the frequency band can be broadened, thereby allowing a high-resolution, diagnostic image to be obtained. The electrical terminal can be connected at a plurality of areas of the piezoelectric element through the conductive members in the acoustic matching layer that is the composite material. Therefore, an ultrasound probe can be achieved that is highly reliable and has excellent operability.

According to the seventh embodiment, when the conductive members 20 and the insulating members or semiconductive members 21 are arrayed in an alternating manner at almost even intervals, as shown in FIG. 7A, is described. However, similar effects can be achieved at random intervals or in a random array.

According to the seventh embodiment, a configuration is described in which, to exchange electrical signals with the ground electrode 5 of the piezoelectric element 1, the electrical terminal 9 for grounding is provided on the front surface of the acoustic matching layer 2, with the acoustic matching layer 2 between the electrical terminal 9 for grounding and the ground electrode 5. However, instead, similar effects can be achieved by a configuration in which the conductive member is formed on both surfaces or on one surface of the acoustic matching layer 2 in the Z direction by sputtering, plating, printing, or the like, and the electrical terminal 9 for grounding is connected to this area.

According to the seventh embodiment, as the acoustic matching layer 2, a coupled structure is used including the conductive member 20 and the insulating member or semiconductive member 21 each made of one type of material. However, similar effects can clearly be achieved even when at least one of the conductive member 20 and the insulating member or semiconductive member 21 is made of two types of materials or more. The structure is not limited to a coupled structure including one type of material for each member.

According to the seventh embodiment, the electrode on the front surface of the piezoelectric element 1 is the ground electrode 5. The electrical terminal 9 for grounding is disposed on the subject side of the ground electrode 5. The electrode on the back surface of the piezoelectric element 1 is the signal electrode 6, and the electrical terminal 7 for signals is in contact with the signal electrode 6. However, the ultrasonic waves can, in principle, be transmitted and received even when, instead, the electrode on the front surface of the piezoelectric element 1 is the signal electrode 6, the electrical terminal 7 for signals is disposed on the subject side of the signal electrode 6, the electrode on the back surface of the piezoelectric element 1 is the ground electrode 5, and the electrical terminal 9 for grounding is in contact with the ground electrode 5.

Figure 7B:
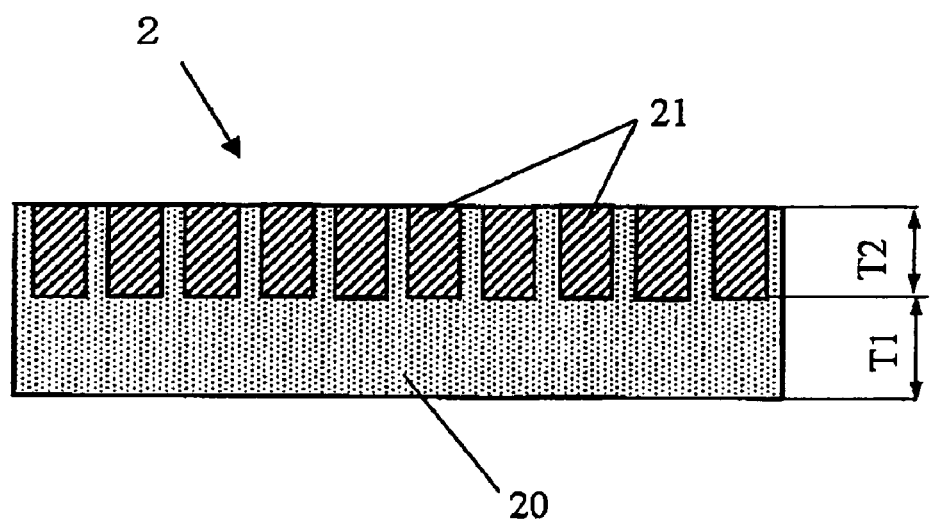
FIG. 7B is a cross-sectional view of another configuration example of an acoustic matching layer configuring the ultrasound probe according to the seventh embodiment of the present invention.

Another configuration example of the acoustic matching layer 2 according to the seventh embodiment is shown in FIG. 7B. The two-layer acoustic matching layers T1 and T2, as shown in FIG. 7A, are configured in the acoustic matching layer 2 shown in FIG. 7B. However, in FIG. 7B, the conductive member 20 occupies 100% of the thickness T1 area. A member, such as an insulating or semiconductive member, having an acoustic impedance value that differs from that of the conductive member 20 is provided in the thickness T2 area with an arbitrary volume amount. For example, a first acoustic matching layer is formed by a material that is graphite filled with a metallic powder, such as copper or silver, being used as the conductive member 20, the acoustic impedance being a value of 6 to 16 MRayl, and the conductive member 20 occupying 100% of the thickness T1. In the thickness T2 area, grooves are formed on the conductive member 20 such as to obtain a desired acoustic impedance. A second acoustic matching layer is formed by a material having a low acoustic impedance (1 to 3 MRayl), such as epoxy resin, urethane, or silicone rubber, serving as the insulating member filling the grooves. The acoustic impedance of the thickness T2 is obtained based on the volume amounts of the conductive member 20 and the insulating or semiconductive member 21. As a result of a configuration such as this being used, similar effects as those according to the embodiment shown in FIG. 7A can be achieved, because the conductive member 20 is connected in the thickness direction of T1 and T2. In FIG. 7B, a configuration is described for a two-layer acoustic matching layer. However, an acoustic matching layer of two or more layers or, in other words, three or more layers can also be configured. The acoustic matching layer is not limited to a two-layer acoustic matching layer.

<Eighth Embodiment>

Figure 8:
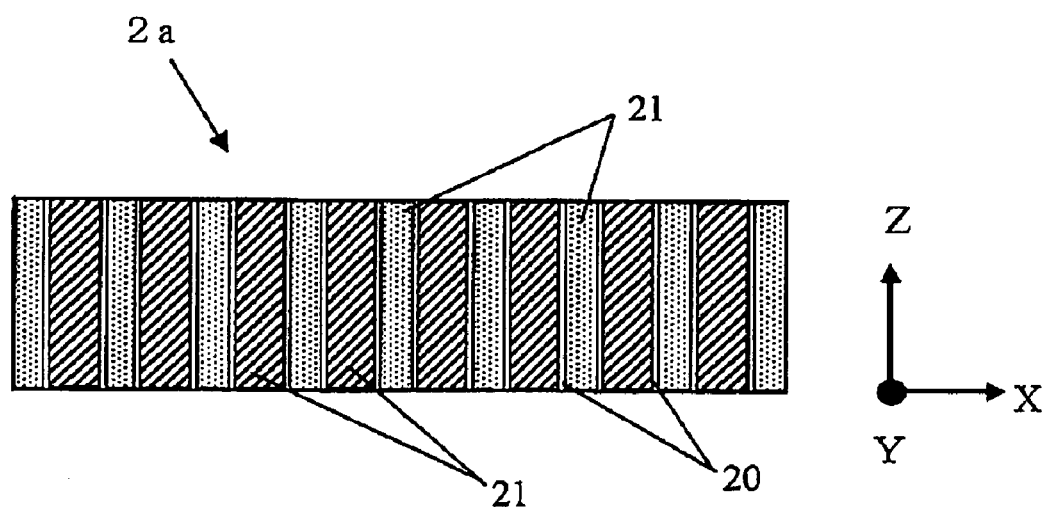
FIG. 8 is a cross-sectional view of a configuration of an acoustic matching layer configuring an ultrasound probe according to an eighth embodiment of the present invention.
Figure 9:
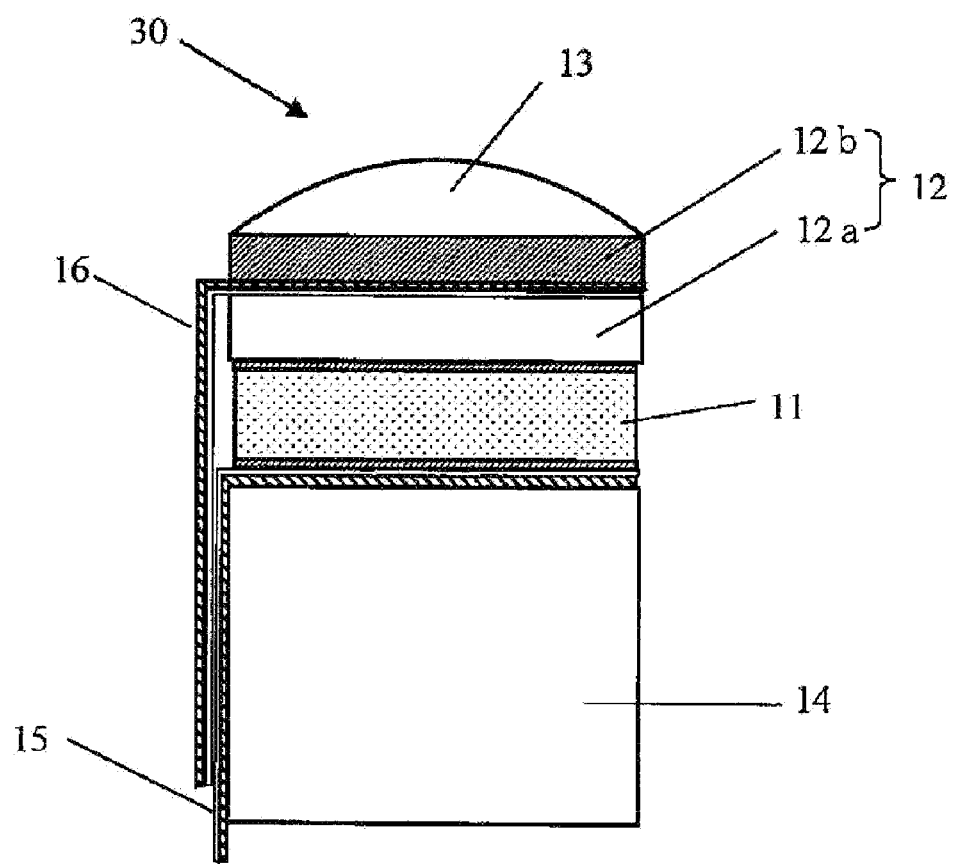
FIG. 9 is a cross-sectional view of a configuration example of a conventional ultrasound probe.

FIG. 8 is a cross-sectional view of a configuration of an acoustic matching layer configuring an ultrasound probe according to an eighth embodiment of the present invention. A rough cross-sectional view of the ultrasound probe is the same as that in FIG. 2A described according to the second embodiment, aside from a difference in the configuration of the first acoustic matching layer 2a. Therefore, the ultrasound probe will be described with reference to FIG. 2A. The first acoustic matching layer section will be described with reference to FIG. 8.

In FIG. 2A, the ultrasound probe 10B includes the plate-shaped piezoelectric element 1, the two-layer acoustic matching layer 2 (2a and 2b) laminated on the front surface (upper side in FIG. 2A) of the piezoelectric element 1, the backing material 3 mounted on the back surface (lower side in FIG. 2A) of the piezoelectric element 1 as required, and the acoustic lens 4 mounted on the front surface of the acoustic matching layer 2 (2a and 2b), also as required. Respective functions of these constituent elements are similar to the functions of the elements configuring a conventional ultrasound probe. Constituent elements and operations of the ultrasound probe 10B are described according to the second embodiment. Therefore, descriptions thereof are omitted.

As the first acoustic matching layer 2a configured by a composite material including a conductive member and an insulating member or semiconductive member, a material is selected such that the acoustic impedance of the first acoustic matching layer 2a is an intermediate value between respective acoustic impedances of the piezoelectric element 1 and the second acoustic matching layer 2b. As the first acoustic matching layer 2a, a configuration example of the conductive member and a plurality of insulating members or semiconductive members of the first acoustic matching layer 2a is shown in FIG. 8. In FIG. 8, a direction in which the ultrasonic waves are emitted towards the subject is a Z direction. Two directions perpendicular to the Z direction are respectively an X direction and a Y direction.

The first acoustic matching layer 2a shown in FIG. 8 is a coupled structure in which the conductive members 20 and the plurality of insulating members or semiconductive members 21 are alternately disposed in the X direction. Here, two types of insulating members or semiconductive members 21 are provided. The conductive members 20 are connected in at least the Z direction. In the configuration in FIG. 8, the width (volume) of the conductive members 20 is significantly narrower than the width (volume) of the two-types of insulating members or semiconductive members 21.

In the configuration, the acoustic impedance of the first acoustic matching layer 2a can be arbitrarily set by the volume amounts (width in the X direction in FIG. 8) of the two types of insulating members or semiconductive members 21 being changed. The conductive member 20 has a significantly smaller value or, in other words, has a significantly narrower width in the X direction in FIG. 8 than the volume amount of the two types of insulating members or semiconductive members 21. The conductive member 20 contributes little to the variations in acoustic impedance. For example, a silicon monocrystal and epoxy resin are used as the two types of insulating members or semiconductive members 21, and respective widths in the X direction are 0.1 millimeters. A silicon monocrystal or epoxy resin on a side surface of which copper, silver, gold, or the like is formed by a method such as plating or sputtering is used as the conductive member 20, and the width is 0.002 millimeters. A percentage of the width of the conductive member 20 within a total width of the two types of insulating members or semiconductive members 21 and the conductive member 20 is about 1%. Contribution to the variations in acoustic impedance is extremely small. Therefore, the function provided by the conductive member 20 is mainly electrical connection from the electrode surface of the piezoelectric element 1. When a configuration such as this is used, manufacturing is facilitated and becomes more precise. Moreover, when metal is used as the conductive member, a disadvantage in that processing is difficult during manufacture of the ultrasound probe can be resolved.

Even when the width of the conductive member 20 increases, the acoustic impedance can be arbitrarily selected through selection of the volume amounts by the percentage of the widths of the three types of members, including the two types of insulating members or semiconductive members 21, being changed. Therefore, the width of the conductive member is not limited.

As shown in FIG. 2A, a configuration is used in which the conductive members 20 of the acoustic matching layer 2a are electrically connected to one electrode of the piezoelectric element 1. The conductive film 9b of the electrical terminal 9 for grounding is in contact with the outer surface of the conductive members 20, and the conductive film 9b and the conductive members 20 are electrically connected. Signals are received and taken out from the electrical terminal 9 for grounding.

As described above, as a result of the composite material including the conductive member and the plurality of insulating members or semiconductive members being provided as the acoustic matching layer provided on the subject side of the piezoelectric element, as described above, the desired acoustic impedance of the acoustic matching layer can be changed as desired. As a result, the frequency band can be broadened, thereby allowing a high-resolution, diagnostic image to be obtained. The electrical terminal can be connected at a plurality of areas of the piezoelectric element through the conductive members in the acoustic matching layer that is the composite material. Therefore, an ultrasound probe can be achieved that is highly reliable and has excellent operability.

According to the eighth embodiment, when the conductive members 20 and the plurality of insulating members or semiconductive members 21 are arrayed in an alternating manner at almost even intervals, as shown in FIG. 8, is described. However, similar effects can be achieved at random intervals or in a random array.

According to the eighth embodiment, a configuration is described in which, to exchange electrical signals with the ground electrode 5 of the piezoelectric element 1, the electrical terminal 9 for grounding is provided on the front surface of the acoustic matching layer 2a, with the acoustic matching layer 2a between the electrical terminal 9 for grounding and the ground electrode 5. However, instead, similar effects can be achieved by a configuration in which the conductive member is formed on both surfaces or on one surface of the acoustic matching layer 2a in the Z direction by sputtering, plating, printing, or the like, and the electrical terminal 9 for grounding is connected to this area.

According to the eighth embodiment, as the acoustic matching layer 2a, a coupled structure is used including the conductive member 20 and two types of insulating member or semiconductive member 21 each made of one type of material. However, similar effects can clearly be achieved by a coupled structure including a plurality of conductive members 20 and insulating members or semiconductive members 21 or a plurality of types of coupled structures being formed.

According to the eighth embodiment, when the conductive members 20 and the plurality of insulating members or semiconductive members 21, shown in FIG. 8, are formed having uniform widths in the Z direction is described. However, similar effects can be achieved by a configuration described according to the sixth embodiment in which the width of the insulating members or semiconductive members 21 continuously changes in the Z direction, forming a so-called wedge shape and the acoustic impedance continuously changes. The conductive members can be formed on the side surfaces of the gradient. Alternatively, similar effects can be achieved by a configuration according to the seventh embodiment in which the width of the insulating members or semiconductive members 21 is changed in stages and the acoustic impedance changes. The conductive members 20 can be provided on the side surfaces.

According to the eighth embodiment, as the first acoustic matching layer 2a of the two-layer acoustic matching layer, a coupled structure including the conductive member 20 and two types of insulating members or semiconductive members 21 each made of one type of material is used. However, similar effects can be achieved when the coupled structure is used in each layer when an acoustic matching layer including three or more layers is provided.

Industrial Applicability

In the ultrasound probe of the present invention, the acoustic impedance of the acoustic matching layer laminated on one electrode formation surface of the piezoelectric element can be set to a desired value. Therefore, frequency band can be broadened, thereby allowing a high-resolution, diagnostic image to be obtained. The electrical terminal can be connected at a plurality of areas on the one electrode formation surface of the piezoelectric element through the acoustic matching layer. Therefore, reliability is enhanced. The ultrasound probe is suitable for various medical fields in which ultrasonic diagnosis is performed on a subject, such as a human body. Moreover, the ultrasound probe can be used in industrial fields for the purpose of performing internal flaw detection on materials and structures.

The invention claimed is:

1. An ultrasound probe comprising:
   a piezoelectric element on which an electrode is formed on both surfaces in a thickness direction; and
   an acoustic matching layer laminated on one electrode formation surface of the piezoelectric element, wherein
   the acoustic matching layer is configured by a composite material made of a plurality of materials including at least a conductive member in an area directly above the piezoelectric element, and
   the conductive member has portions penetrating in a layer thickness direction at a plurality of sections in the area on the one electrode formation surface of the piezoelectric element.

2. The ultrasound probe according to claim 1, wherein the acoustic matching layer is configured by a composite material made of a plurality of materials including the insulating member or semiconductive member and a conductive member, or a composite material made of a plurality of materials including the insulating member or semiconductive member and a plurality of materials including the conductive member.

3. An ultrasound probe comprising:
a plurality of piezoelectric elements having a predetermined thickness, on which an electrode is formed on both surfaces in a thickness direction, and which are disposed in a direction perpendicular to the thickness direction; and
a plurality of acoustic matching layers laminated on one electrode formation surface of the plurality of piezoelectric elements, wherein
the acoustic matching layer includes a first acoustic matching layer and a second acoustic matching layer successively laminated on the piezoelectric elements,
the first acoustic matching layer is configured by a composite material made of a plurality of materials including an insulating member or semiconductive member and a conductive member, and
the conductive member has portions penetrating in a layer thickness direction at a plurality of sections on the one electrode formation surface of the piezoelectric element.

4. The ultrasound probe according to any one of claims 1 to 3, wherein, in the composite material configuring the acoustic matching layer adjacent to the piezoelectric element, the insulating member or semiconductive member and the conductive member are disposed in predetermined areas.

5. The ultrasound probe according to any one of claims 1 to 3, comprising:
an electrical terminal that is laminated on an outer surface section of the acoustic matching layer adjacent to the piezoelectric element, wherein
in the electrical terminal, a conductive film is deposited on one main surface of an insulating film, the electrical terminal is laminated such that the one main surface of the insulating film faces the acoustic matching layer, and the conductive film is electrically connected to one electrode formed on the piezoelectric element, via the conductive member configuring the acoustic matching layer.

6. An ultrasound probe comprising:
a plurality of piezoelectric elements having a predetermined thickness, on which an electrode is formed on both surfaces in a thickness direction, and which are disposed in a direction perpendicular to the thickness direction; and
a plurality of acoustic matching layers laminated on one electrode formation surface of the plurality of piezoelectric elements, wherein
with n as an integer of three or more, the acoustic matching layer includes a first to n-th matching layers successively laminated on the piezoelectric elements, and an electrical terminal is inserted between the first acoustic matching layer and a second acoustic matching layer,
at least the first acoustic matching layer is configured by a composite material made of a plurality of materials including an insulating member or semiconductive member and a conductive member, and the conductive member has portions penetrating in a layer thickness direction at a plurality of sections on the one electrode formation surface of the piezoelectric elements, and
in the electrical terminal, a conductive film is deposited on an insulating film, the electrical terminal is laminated such that one main surface of the insulating film faces the acoustic matching layer, and the conductive film is electrically connected to one electrode formed on the piezoelectric element, via the conductive member configuring the first acoustic matching layer.

7. An ultrasound probe comprising:
a plurality of piezoelectric elements having a predetermined thickness, on which an electrode is formed on both surfaces in a thickness direction, and which are disposed in a direction perpendicular to the thickness direction; and
a plurality of acoustic matching layers laminated on one electrode formation surface of the plurality of piezoelectric elements, wherein
with n as an integer of three or more, the acoustic matching layer includes a first to n-th matching layers successively laminated on the piezoelectric elements, and an electrical terminal is inserted between the second acoustic matching layer and a third acoustic matching layer,
at least the first acoustic matching layer and the second acoustic matching layer is configured by a composite material made of a plurality of materials including an insulating member or semiconductive member and a conductive member, and the conductive member has portions penetrating in a layer thickness direction at a plurality of sections on the one electrode formation surface of the piezoelectric elements, and
in the electrical terminal, a conductive film is deposited on an insulating film, the electrical terminal is laminated such that one main surface of the insulating film faces the acoustic matching layer, and the conductive film is electrically connected to one electrode formed on the piezoelectric element, via the conductive member configuring the first acoustic matching layer and the conductive member configuring the second acoustic matching layer.

8. The ultrasound probe according to claim 6 or 7, wherein, in the composite material configuring the first acoustic matching layer, the insulating member or semiconductive member and the conductive member are disposed in predetermined areas.

9. The ultrasound probe according to claim 7, wherein, in the composite material configuring the second acoustic matching layer, the insulating member or semiconductive member and the conductive member are disposed in predetermined areas.

10. The ultrasound probe according to claim 2, wherein, with a thickness direction of the piezoelectric element as a Z direction, a direction perpendicular to the Z direction as an X direction, and a direction perpendicular to the Z direction and the X direction as a Y direction, the composite material configuring the acoustic matching layer has any one coupled structure among a coupled structure in which the conductive member has a connection in only the Z direction and has no connection in the X and Y directions, and the insulating member or semiconductive member has a connection in three directions, X, Y, and Z,
a coupled structure in which the conductive member has a connection in two directions, Y and Z, and the insulating member or semiconductive member has a connection in two directions, Y and Z, or
a coupled structure in which the conductive member has a connection in three directions, X, Y, and Z, and the insulating member or semiconductive member has a connection in only the Z direction and has no connection in the X and Y directions.

11. An ultrasound probe comprising:
a piezoelectric element having a predetermined thickness and on which an electrode is formed on both surfaces in a thickness direction; and
an acoustic matching layer laminated on one electrode formation surface of the piezoelectric element, wherein
the acoustic matching layer is configured by a composite material made of a plurality of materials including at least a conductive member in an area directly above the piezoelectric element,
the conductive member has portions penetrating in a layer thickness direction at a plurality of sections in the area on the one electrode formation surface of the piezoelectric element, and
the conductive member is configured such that a volume amount is a continuous gradient in a thickness direction or the volume amount changes in stages.

12. The ultrasound probe according to claim 11, wherein the composite material made of the plurality of materials of the acoustic matching layer is configured by a material including the insulating member or semiconductive member and a conductive member.

13. The ultrasound probe according to claim 1, wherein the conductive member in the composite material includes at least one of metal, a composite of metal and a high-polymer material, and carbide of graphite.

14. The ultrasound probe according to claim 2, wherein the insulating member or semiconductive member in the composite material is at least one of glass, ceramics, quartz crystal, a composite of organic polymer and metal, and a monocrystal or polycrystal silicon.

15. An ultrasound probe comprising:
a piezoelectric element on which an electrode is formed on both surfaces in a thickness direction; and
an acoustic matching layer laminated on one electrode formation surface of the piezoelectric element, wherein
the acoustic matching layer is configured by a composite material made of a plurality of materials including at least a conductive member, and
the conductive member has portions penetrating in a layer thickness direction at a plurality of sections on the one electrode formation surface of the piezoelectric element,
wherein the acoustic matching layer is configured by a composite material made of a plurality of materials including an insulating member or semiconductive member and a conductive member, or a composite material made of a plurality of materials including the insulating member or semiconductive member and a plurality of materials including the conductive member.

16. An ultrasound probe comprising:
a piezoelectric element on which an electrode is formed on both surfaces in a thickness direction; and
an acoustic matching layer laminated on one electrode formation surface of the piezoelectric element, wherein
the acoustic matching layer is configured by a composite material made of a plurality of materials including at least a conductive member, and
the conductive member has portions penetrating in a layer thickness direction at a plurality of sections on the one electrode formation surface of the piezoelectric element,
wherein the conductive member in the composite material includes at least one of metal, a composite of metal and a high-polymer material, and carbide of graphite.

17. The ultrasound probe according to claim 15, wherein the insulating member or semiconductive member in the composite material is at least one of glass, ceramics, quartz crystal, a composite of organic polymer and metal, and a monocrystal or polycrystal silicon.

18. An ultrasound probe comprising:
a piezoelectric element having a predetermined thickness and on which an electrode is formed on both surfaces in a thickness direction; and
an acoustic matching layer laminated on one electrode formation surface of the piezoelectric element, wherein
the acoustic matching layer is configured by a composite material made of a plurality of materials including at least a conductive member,
the conductive member has portions penetrating in a layer thickness direction at a plurality of sections on the one electrode formation surface of the piezoelectric element, and
the conductive member is configured such that a volume amount is a continuous gradient in a thickness direction or the volume amount changes in stages,
wherein the composite material made of the plurality of materials of the acoustic matching layer is configured by a material including an insulating member or semiconductive member and a conductive member.

19. The ultrasound probe according to claim 15, wherein, with a thickness direction of the piezoelectric element as a Z direction, a direction perpendicular to the Z direction as an X direction, and a direction perpendicular to the Z direction and the X direction as a Y direction, the composite material configuring the acoustic matching layer has any one coupled structure among a coupled structure in which the conductive member has a connection in only the Z direction and has no connection in the X and Y directions, and the insulating member or semiconductive member has a connection in three directions, X, Y, and Z,
a coupled structure in which the conductive member has a connection in two directions, Y and Z, and the insulating member or semiconductive member has a connection in two directions, Y and Z, or
a coupled structure in which the conductive member has a connection in three directions, X, Y, and Z, and the insulating member or semiconductive member has a connection in only the Z direction and has no connection in the X and Y directions.

20. An ultrasound probe comprising:
a piezoelectric element on which an electrode is formed on both surfaces in a thickness direction; and
an acoustic matching layer laminated on one electrode formation surface of the piezoelectric element, wherein
the acoustic matching layer is configured by a composite material made of a plurality of materials including at least a conductive member and an insulating member or semiconductive member opposite to the piezoelectric element side,
the conductive member has a portion penetrating in a layer thickness direction, and
the conductive member is configured such that a volume amount changes in stages in a thickness direction.

21. The ultrasound probe according to claim 1, wherein the acoustic matching layer includes one of an insulating member or semiconductive member.

22. The ultrasound probe according to claim 11, wherein the acoustic matching layer includes one of an insulating member or semiconductive member.

* * * * *

UNITED STATES PATENT AND TRADEMARK OFFICE
CERTIFICATE OF CORRECTION

| | | |
|---|---|---|
| PATENT NO. | : 8,319,399 B2 | Page 1 of 1 |
| APPLICATION NO. | : 12/447535 | |
| DATED | : November 27, 2012 | |
| INVENTOR(S) | : Koetsu Saito | |

It is certified that error appears in the above-identified patent and that said Letters Patent is hereby corrected as shown below:

On the Title page, item (73) Assignee, please delete "Oskak" and instead insert --Osaka--

Signed and Sealed this
Ninth Day of July, 2013

Teresa Stanek Rea
*Acting Director of the United States Patent and Trademark Office*